United States Patent
Wu et al.

(10) Patent No.: US 8,658,361 B2
(45) Date of Patent: Feb. 25, 2014

(54) ULTRA SENSITIVE METHOD FOR IN SITU DETECTION OF NUCLEIC ACIDS

(75) Inventors: Xingyong Wu, Pleasanton, CA (US); Huei-Yu Fay Wang, San Francisco, CA (US); Nan Su, San Ramon, CA (US); Li-Chong Wang, Foster City, CA (US); Yuling Luo, San Ramon, CA (US)

(73) Assignee: Advanced Cell Diagnostics, Inc., Hayward, CA (US)

( * ) Notice: Subject to any disclaimer, the term of this patent is extended or adjusted under 35 U.S.C. 154(b) by 0 days.

(21) Appl. No.: 13/278,353

(22) Filed: Oct. 21, 2011

(65) Prior Publication Data

US 2012/0100540 A1 Apr. 26, 2012

Related U.S. Application Data

(60) Provisional application No. 61/405,503, filed on Oct. 21, 2010, provisional application No. 61/412,276, filed on Nov. 10, 2010.

(51) Int. Cl.

| | |
|---|---|
| *C12Q 1/68* | (2006.01) |
| *C12Q 1/00* | (2006.01) |
| *G01N 33/53* | (2006.01) |
| *C12Q 1/28* | (2006.01) |
| *C12P 19/34* | (2006.01) |
| *C12M 1/34* | (2006.01) |
| *B01L 3/00* | (2006.01) |
| *G01N 31/22* | (2006.01) |
| *C07H 21/02* | (2006.01) |
| *C07H 21/04* | (2006.01) |

(52) U.S. Cl.
USPC ............... 435/6.1; 435/4; 435/7.7; 435/7.91; 435/28; 435/91.1; 435/287.2; 422/68.1; 422/82.05; 422/82.07; 422/430; 536/23.1; 536/24.3

(58) Field of Classification Search
USPC ............ 435/4, 6.1, 7.7, 7.94, 28, 91.1, 287.2; 422/68.1, 82.05, 82.07, 430; 536/23.1, 536/24.3
See application file for complete search history.

(56) References Cited

U.S. PATENT DOCUMENTS

| | | | |
|---|---|---|---|
| 4,868,105 | A | 9/1989 | Urdea et al. |
| 4,888,278 | A | 12/1989 | Singer et al. |

(Continued)

FOREIGN PATENT DOCUMENTS

| | | |
|---|---|---|
| EP | 0795610 | 9/1997 |
| EP | 1 428 892 B1 | 11/2006 |

(Continued)

OTHER PUBLICATIONS

Speel et al, Tyramide Signal Amplification for DNA and mRNA in Situ Hybridization, 2006, Methods in Molecular Biology, 326, 33-60.*

(Continued)

*Primary Examiner* — Narayan Bhat
(74) *Attorney, Agent, or Firm* — Jones Day (57) ABSTRACT

Disclosed is a method for in situ detection of one or more target nucleic acids based on a combination of an in situ hybridization (ISH) assay method and a general ISH signal amplification method. This new method produces high signal intensity and while keeps low background noise of signal amplification. The result can be consistently reproduced and the method can be easily adopted for routine clinic diagnostic use. Further, the invention relates to a kit, comprising the components of the ISH assay and a general ISH signal amplification assay, for sensitive detection of one or more target nucleic acids.

60 Claims, 5 Drawing Sheets

(56) References Cited

U.S. PATENT DOCUMENTS

| | | | |
|---|---|---|---|
| 5,093,232 A | 3/1992 | Urdea et al. |
| 5,122,599 A | 6/1992 | Barnett et al. |
| 5,124,246 A | 6/1992 | Urdea et al. |
| 5,185,244 A | 2/1993 | Wallace |
| 5,198,357 A | 3/1993 | Holmovist et al. |
| 5,334,499 A | 8/1994 | Burdick et al. |
| 5,374,524 A | 12/1994 | Miller |
| 5,393,672 A | 2/1995 | Ness et al. |
| 5,523,204 A | 6/1996 | Singer et al. |
| 5,543,305 A | 8/1996 | Cummins et al. |
| 5,571,670 A | 11/1996 | Urdea et al. |
| 5,614,362 A | 3/1997 | Urdea et al. |
| 5,624,802 A | 4/1997 | Urdea et al. |
| 5,633,134 A | 5/1997 | Shuber |
| 5,635,352 A | 6/1997 | Urdea et al. |
| 5,643,715 A | 7/1997 | Lancaster et al. |
| 5,681,697 A | 10/1997 | Urdea et al. |
| 5,681,702 A | 10/1997 | Collins et al. |
| 5,728,527 A | 3/1998 | Singer et al. |
| 5,747,244 A | 5/1998 | Sheridan et al. |
| 5,780,227 A | 7/1998 | Sheridan et al. |
| 5,804,684 A | 9/1998 | Su |
| 5,849,481 A | 12/1998 | Urdea et al. |
| 5,866,331 A | 2/1999 | Femino et al. |
| 5,888,778 A | 3/1999 | Shuber |
| 5,945,515 A | 8/1999 | Chomczynski |
| 5,985,549 A | 11/1999 | Singer et al. |
| 6,007,994 A | 12/1999 | Ward et al. |
| 6,221,589 B1 | 4/2001 | Lane et al. |
| 6,232,462 B1 | 5/2001 | Collins et al. |
| 6,242,184 B1 | 6/2001 | Singer et al. |
| 6,261,779 B1 * | 7/2001 | Barbera-Guillem et al. | 435/6.11 |
| 6,268,147 B1 | 7/2001 | Beattie et al. |
| 6,306,643 B1 | 10/2001 | Gentalen et al. |
| 6,352,827 B1 | 3/2002 | Lin et al. |
| 6,418,382 B2 | 7/2002 | Rothberg et al. |
| 6,428,957 B1 | 8/2002 | Delenstarr |
| 6,503,714 B1 * | 1/2003 | Weindel et al. | 435/6.12 |
| 6,610,475 B1 | 8/2003 | Kacian et al. |
| 6,670,464 B1 | 12/2003 | Shimkets et al. |
| 6,673,914 B1 | 1/2004 | Hoon |
| 6,852,490 B2 | 2/2005 | Gentalen et al. |
| 7,033,758 B2 | 4/2006 | Kenny et al. |
| 7,064,197 B1 | 6/2006 | Rabbani et al. |
| 7,524,631 B2 | 4/2009 | Patterson et al. |
| 7,615,351 B2 | 11/2009 | McMaster |
| 7,709,198 B2 | 5/2010 | Luo et al. |
| 7,803,541 B2 | 9/2010 | Luo et al. |
| 7,888,032 B2 | 2/2011 | Patterson et al. |
| 7,927,798 B2 | 4/2011 | Zheng et al. |
| 7,951,539 B2 | 5/2011 | McMaster et al. |
| 7,968,327 B2 | 6/2011 | McMaster et al. |
| 8,017,360 B2 | 9/2011 | Luo et al. |
| 8,470,563 B2 | 6/2013 | Kermekchiev et al. |
| 2002/0034753 A1 | 3/2002 | Yang et al. |
| 2002/0034754 A1 | 3/2002 | Reed et al. |
| 2002/0106644 A1 | 8/2002 | Rosenow |
| 2002/0172950 A1 | 11/2002 | Kenny et al. |
| 2002/0172953 A1 | 11/2002 | Mirkin et al. |
| 2002/0187470 A1 | 12/2002 | Casey et al. |
| 2003/0165935 A1 | 9/2003 | Vann et al. |
| 2003/0170613 A1 | 9/2003 | Straus et al. |
| 2003/0211489 A1 | 11/2003 | Shen et al. |
| 2004/0023248 A1 | 2/2004 | O'Malley |
| 2004/0072231 A1 | 4/2004 | Mirkin et al. |
| 2004/0076954 A1 | 4/2004 | Caldwell et al. |
| 2004/0086930 A1 | 5/2004 | Tereba et al. |
| 2004/0115686 A1 | 6/2004 | Dolginow et al. |
| 2004/0265934 A1 | 12/2004 | Stender et al. |
| 2005/0009063 A1 | 1/2005 | Xia et al. |
| 2005/0037397 A1 | 2/2005 | Mirkin et al. |
| 2005/0170370 A1 | 8/2005 | Rabbani et al. |
| 2005/0282220 A1 | 12/2005 | Prober et al. |
| 2006/0172284 A1 | 8/2006 | Zheng et al. |
| 2006/0263769 A1 | 11/2006 | Luo et al. |
| 2007/0015188 A1 | 1/2007 | Luo et al. |
| 2008/0008994 A1 | 1/2008 | Stender et al. |
| 2008/0038725 A1 | 2/2008 | Luo et al. |
| 2009/0081688 A1 | 3/2009 | Luo et al. |
| 2009/0298709 A1 | 12/2009 | Ma |
| 2010/0081131 A1 | 4/2010 | Ach et al. |
| 2011/0059442 A1 | 3/2011 | Luo et al. |
| 2011/0059866 A1 | 3/2011 | Luo et al. |
| 2011/0105351 A1 | 5/2011 | Luo et al. |
| 2011/0171644 A1 | 7/2011 | Luo et al. |
| 2011/0223606 A1 | 9/2011 | McMaster et al. |
| 2011/0256536 A1 | 10/2011 | McMaster et al. |
| 2012/0003648 A1 | 1/2012 | Ma et al. |
| 2012/0004132 A1 | 1/2012 | Zhang et al. |
| 2012/0009577 A1 | 1/2012 | Luo et al. |
| 2012/0052498 A1 | 3/2012 | Nguyen et al. |
| 2012/0071343 A1 | 3/2012 | Ma et al. |
| 2012/0157348 A1 | 6/2012 | Zheng et al. |
| 2012/0172246 A1 | 7/2012 | Nguyen et al. |
| 2012/0178081 A1 | 7/2012 | Nguyen et al. |
| 2012/0214152 A1 | 8/2012 | Ma et al. |
| 2013/0023433 A1 | 1/2013 | Luo |
| 2013/0171621 A1 | 7/2013 | Luo |

FOREIGN PATENT DOCUMENTS

| | | |
|---|---|---|
| WO | WO 94/00597 | 1/1994 |
| WO | WO 94/00598 A1 | 1/1994 |
| WO | WO 01/83814 | 8/2001 |
| WO | WO 01/94632 A2 | 12/2001 |
| WO | WO 03/57914 A2 | 7/2003 |
| WO | WO 2004/020654 A2 | 3/2004 |
| WO | WO 2006/002433 | 1/2006 |
| WO | WO 2006/124771 A2 | 11/2006 |
| WO | WO 2007/001986 | 1/2007 |
| WO | WO 2007/002006 | 1/2007 |
| WO | WO 2010/060103 A1 | 5/2010 |
| WO | WO 2010/129941 A1 | 11/2010 |
| WO | WO 2011/038403 A1 | 3/2011 |
| WO | WO 2011/094669 A1 | 8/2011 |
| WO | WO 2012/040168 A2 | 3/2012 |
| WO | WO 2012/054795 A1 | 4/2012 |
| WO | WO 2012/103414 A2 | 8/2012 |
| WO | WO 2013/134442 A1 | 9/2013 |

OTHER PUBLICATIONS

Zheng et al, Sensitive and Quantitative Measurement of Gene Expression Directly from a Small Amount of Whole Blood, 2006, 52, 1294-1302.*

Wang et al, RNAscope, A Novel in Situ RNA Analysis Platform for Formalin-Fixed, Paraffin-Embedded Tissues, 2012, The Journal of Molecular Diagnostics, 14, 22-29.*

Bobrow MN et al, 2000, "Unit 8.9 Tyramide Signal Amplification (TSA) Systems for the Enhancement of ISH Signals in Cytogenetics". Current Protocols in Cytometry. John Wiley & Sons. Inc. US. No. supplement 11. pp. 8.9.1-8.9.16.

Lizard G et al, 2001, "In Situ Hybridization Detection of Single-Copy Human Papillomavirus on Isolated Cells. Using a Catalyzed Signal Amplification System: Genpoint" Diagnostic Cytopathology, vol. 24. No. 2. pp. 112-116.

Deichmann et al, 1997, "Ultra-sensitive FISH is a useful tool for studying chronic HIV-1 infection". Journal of Virological Methods. vol. 65. No. 1. pp. 19-25.

Ahern, "Biochemical, Reagents Kits Offer Scientists Good Return on Investment," The Scientist, 9:1-4 (1995).

Alexandrescu et al., "Melanoma-Specific Marker Expression in Skin Biopsy Tissues as a Tool to Facilitate Melanoma Diagnosis," The Journal of Investigative Dermatology, 130(7): 1887-1892 (2010).

Al-Soud et al. "A sample preparation method which facilitates detection of bacteria in blood cultures by the polymerase chain reaction," *J. Microbiol. Meth.*, 32:217-224 (1998).

Ang et al., "Human papillomavirus and survival of patients with oropharyngeal cancer," *N. Engl. J. Med.*, 363(1):24-35 (2010).

Application Note from Amersham Biosciences, "Whole genome amplification from crude blood lysates," 2003 (4 pages).

(56) References Cited

OTHER PUBLICATIONS

Application Note from Applied Biosystems, "Total RNA purification from whole blood," 2002 (6 pages).
Bach et al. "Magnetic capture-hybridization method for purification and probing of mRNA for neutral protease of *Bacillus cereus*," *J. Microbiol. Methods*, 37(2):187-192 (1999).
Balnaves et al., "Direct PCR from CVS and blood lysates for detection of cystic fibrosis and Duchenne muscular dystrophy deletions," *Nucl. Acids. Res.*, 19(5):1155 (1991).
Bortolin et al., "Analytical validation of the tag-it high-throughput microsphere-based universal array genotyping platform: application to the multiplex detection of a panel of thrombophilia-associated single-nucleotide polymorphisms," *Clin. Chem.*, 50(11):2028-2036 (2004).
Borucki et al., "Suspension microarray with dendrimer signal amplification allows direct and high-throughput subtyping of Listeria monocytogenes from genomic DNA," *J. Clin. Microbiol.*, 43(7):3255-3259 (2005).
Burris et al., "A novel method for analysis of nuclear receptor function at natural promoters: peroxisome proliferator-activated receptor .gamma. agonist actions on aP2 gene expression detected using branched DNA messenger RNA quantitation," *Mol. Endocrinol.*, 13(3):410-417 (1999).
Bushnell et al., "ProbeDesigner: for the design of probesets for branched DNA (bDNA) signal amplification assays," *Bioinformatics*, 15(5):348-355 (1999).
Chung et al., "Human papillomavirus in head and neck cancer: its role in pathogenesis and clinical implications," *Clin. Cancer Res.*, 15:6758-6762 (2009).
Collins et al., "A branched DNA signal amplification assay for quantification of nucleic acid targets below 100 molecules/ml," *Nucl. Acids Res.*, 25(15):2979-2984 (1997).
Collins et al., "Branched DNA (bDNA) technology for direct quantification of nucleic acids: design and performance," in Gene Quantification, F. Ferre, ed., pp. 205-223 (1998).
Conway et al., "Gene Expression Profiling of Paraffin-Embedded Primary Melanoma Using the DASL Assay Identifies Increased Osteopont in Expression as Predictive of Reduced Relapse-Free Survival," Clinical Cancer Research: An Official Journal of the American Association for Cancer Research, 15(22): 6939-6946 (2009).
D'Souza et al., "Case-control study of human papillomavirus and oropharyngeal cancer," *N. Engl. J. Med.*, 356(19):1944-1956 (2007).
De Vries et al., "PCR on cell lysates obtained from whole blood circumvents DNA isolation," *Clin. Chem.*, 47(9):1701-1702 (2001).
Dimitrov et al., "Prediction of hybridization and melting for double-stranded nucleic acids," *Biophysical J.*, 87(1):215-226 (2004).
Flagella et al., "A multiplex branched DNA assay for parallel quantitative gene expression profiling," *Anal. Biochem.*, 352(1):50-60 (2006).
Fulton et al., "Advanced multiplexed analysis with the FlowMetrix system," *Clin. Chem.*, 43(9):1749-1756 (1997).
Gentalen and Chee., "A novel method for determining linkage between DNA sequences: hybridization to paired probe arrays," *Nucl. Acids Res.*, 27(6):1485-1491 (1999).
Haqq et al., "The Gene Expression Signatures of Melanoma Progression," Proceedings of the National Academy of Sciences of USA, 102(17):6092-6097 (2005).
Harlin et al., "Chemokine Expression in Melanoma Metastases associated with CD8+ T-Cell Recruitment," Cancer Research, 69(7): 3077-3085 (2009).
Hartley et al., "Detection of chemical-induced differential expression of rat hepatic cytochrome P450 mRNA transcripts using branched DNA signal amplification technology," *Drug Metabolism and Disposition*, 28(5):608-616 (2000).
Higuchi, "DNA from whole blood for PCR," Amplifications, 2:1-3. [online]. The Jackson Laboratory, 1998. [retrieved on Jul. 24, 2009]. Retrieved from the internet:<URL:http//www.jax.org.imr.whole.sub.--blood.html>.
Hines et al., "Human papillomaviruses: their clinical significance in the management of cervical carcinoma," *Oncology*, 9(4):279-285 (1995).
Ho et al., "Type-specific human papillomavirus oncogene messenger RNA levels correlate with the severity of cervical neoplasia," *Intl. J. Cancer*, 127(3):622-632 (2010).
Iannone, "Multiplexed single nucleotide polymorphism genotyping by oligonucleotide ligation and flow cytometry," *Cytometry*, 39(2): 131-140 (2000).
Ikeda et al., "Characterization of an Antigen that is Recognized on a Melanoma Showing Partial HLA Loss by CTL Expressing an NK Inhibitory Receptor," Immunity, 6(2): 199-208 (1997).
International Search Report and Written Opinion for PCT/US2011/057202 dated Feb. 24, 2012.
Kenny et al., "Detection of viral infection and gene expression in clinical tissue specimens using branched DNA (bDNA) in situ hybridization," *J. Histochem. Cytochem.*, 50(9):1219-1227 (2002).
Kern et al., "An enhanced-sensitivity branched-DNA assay for quantification of human immunodeficiency virus type 1 RNA in plasma," *J. Clin. Microbiol.*, 34(12):3196-3202 (1996).
Kjaer et al., "Long-term absolute risk of cervical intraepithelial neoplasia grade 3 or worse following human papillomavirus infection: role of persistence," *J. Natl. Cancer Inst.*, 102(19):1478-1488 (2010).
Koh et al., "Molecular Classification of Melanomas and Nevi Using Gene Expression Microarray Signatures and Formalin-Fixed and Paraffin-Embedded Tissue," Modern Pathology: An Official Journal of the United States and Canadian Academy of Pathology, 22(4): 538-546 (2009).
Landis et al., "Cancer statistics, 1999," *CA Cancer J. Clin.*, 49(1):8-31 (1999).
Lewin & Stewart-Haynes, "A simple method for DNA extraction from leukocytes for use in PCR," *BioTechniques*, 13(4):522-524 (1992).
Lewis et al., "p16 positive oropharyngeal squamous cell carcinoma: an entity with a favorable prognosis regardless of tumor HPV status," *Am. J. Surg. Pathol.*, 34(8):1088-1096 (2010).
Lo et al., "Fetal DNA in maternal plasma: biology and diagnostic applications," Clin. Chem., 46(12):1903-1906 (2000).
Malygin et al, Hybridization of two oligodeoxynucleotides to both strands of an RNA hairpin structure increases the efficiency of RNA-DNA duplex formation, *FEBS Letters*, 392:114-116 (1996).
Marur et al., "HPV-associated head and neck cancer: a virus-related cancer epidemic," *Lancet Oncol.*, 11(8):781-789 (2010).
Meijer et al., "Clinical utility of HPV genotyping," *Gynecol. Oncol.*, 103(1):12-17 (2006).
Mercier et al., "Direct PCR from whole blood, without DNA extraction," Nucl. Acids. Res., 18(19):5908 (1990).
Mocellin et al., "Molecular Detection of Circulating Tumor Cells in an Independent Prognostic Factor in Patients with High-Risk Cutaneous Melanoma," International Journal of Cancer, 111(5): 741-745 (2004).
Moody et al., "Human papillomavirus oncoproteins: pathways to transformation," *Nat. Rev. Cancer*, 10(8):550-560, 2010.
Narayanan, "Overview of principles and current uses of DNA probes in clinical and laboratory medicine," *Ann. Clin. Lab. Sci.*, 22(6):353-376 (1992).
Naucler et al., "Human papillomavirus and papanicolaou tests to screen for cervical cancer," *N. Engl. J. Med.*, 357(16):1589-1597 (2007).
Nolte, "Branched DNA signal amplification for direct quantitation of nucleic acid sequences in clinical specimens," *Adv. Clin. Chem.*, 33(1):201-235 (1998).
Nordvag et al., "Direct PCR of washed blood cells," *BioTechniques*, 12(4):490-493 (1992).
Ostor, "Natural history of cervical intraepithelial neoplasia: a critical review," *Int. J. Gynecol. Pathol.*, 12(2):186-192 (1993).
Player et al., "Single-copy gene detection using branched DNA (bDNA) in situ hybridization" *J. Histochem. Cytochem.*, 49:603-611 (2001).
Qian et al., "Recent Developments in Signal Amplification Methods for in Situ Hybridization," Diagnostic Molecular Pathology, 12(1): 1-13 (2003).

(56) References Cited

OTHER PUBLICATIONS

Robinson et al., "Refining the diagnosis of oropharyngeal squamous cell carcinoma using human papillomavirus testing," *Oral Oncol.*, 46(7):492-496 (2010).

Schiffman et al., "Human papillomavirus and cervical cancer," *Lancet* 370(9590):890-907 (2007).

Schweitzer & Kingsmore, "Combining nucleic acid amplification and detection," *Curr. Opin. Biotechnol.*, 12(1):21-27 (2001).

Shah et al., "Detection of Mycobacterium tuberculosis directly from spiked human sputum by Q-beta replicase-amplifiied assay," *J. Clin. Microbiol.*, 33(2):322-328 (1995).

Shah et al., "Novel, ultrasensitive, Q-beta, replicase-amplified hybridization assay for detection of Chlamydia trachomatis," *J. Clin. Microbiol.*, 32(11):2718-2724 (1994).

Shah et al., "Ultra-sensitive and specific detections of porcine endogenous retrovirus (PERV) using a sequence-capture real-time PCR approach," *J. Virol.Meth.*, 109:209-216 (2003).

Shen et al., "Quantification of cytokine mRNA in peripheral blood mononuclear cells using branched DNA (bDNA) technology," J. Immunol. Meth., 215(1-2):123-134 (1998).

Shi et al., "Comparitive prognostic value of HPV16 E6 mRNA compared with in situ hybridization for human oropharyngeal squamous carcinoma," *J. Clin. Oncol.*, 27(36):6213-6221 (2009).

Sleijfer et al., "Circulating tumour cell detection on its way to routine diagnostic implementation?" European Journal of Cancer, 43(18):2645-2650 (2007).

Smeets et al., "A novel algorithm for reliable detection of human papillomavirus in paraffin embedded head and neck cancer specimen," *Intl. J. Cancer*, 121(11):2465-2472 (2007).

Solomon et al., "Cervical cancer screening rates in the United States and the potential impact of implementation of screening guidelines," *CA Cancer J. Clin.*, 57(2):105-111 (2007).

Stoler et al., "Interobserver reproducibility of cervical cytologic and histologic interpretations: realistic estimates from the ASCUS-LSIL Triage Study," *JAMA*, 285(11):1500-1505 (2001).

Stone et al., "Detection of rRNA from four respiratory pathogens using an automated Qβ replicase assay," *Mol. Cell. Probes*, 10:359-370 (1996).

Syrjanen, "Spontaneous evolution of intraepithelial lesions according to the grade and type of the implicated human papillomavirus (HPV)," *Eur. J. Obstet. Gynecol. Reprod. Biol.*, 65(1):45-53 (1996).

Thomison et al., "Human papillomavirus: molecular and cytologic/histologic aspects related to cervical intraepithelial neoplasia and carcinoma," *Hum. Pathol.*, 39(2):154-166 (2008).

Tsai et al., "Nucleic acid capture assay, a new method for direct quantitation of nucleic acids," *Nucl. Acids Res.*, 31(6):e25 (2003).

Ugozzoli et al., "Detection of specific alleles by using allele-specific primer extension followed by capture on solid support," *GATA*, 9(4):107-112 (1992).

Van Cleve et al, "Direct quantitation of HIV by flow cytometry using branched DNA signal amplification," *Molecular and Celluar Probes*, 12:243-247 (1998).

Wang et al., "Multiplex Analysis of Gene Expression in Single Cells for Circulating Tumor Cell Detection," Proceedings of the American Association for Cancer Research Annual Meeting, 49: 1224-1225 (2008).

Wang et al., "Regulation of insulin preRNA splicing by glucose," *Proc. Nat. Acad. Sci. USA*, 94(9):4360-4365 (1997).

Well, "Human papillomavirus associated lesions of the lower female genital tract," *Advances in Gynacological Pathology*, Lowe and Fox eds., Churchill Livingstone, United Kingdom, 79-97 (1992).

Wilber & Urdea, "Quantification of HCV RNA in clinical specimens by branched DNA (bDNA) technology," Methods in Molecular Medicine: Hepatitis C 19:71-78 (1998).

Wilson et al., "A multiplexed PCR-coupled liquid bead array for the simultaneous detection of four biothreat agents," *Mol.Cell. Probes*, 19(2):137-144 (2005).

Wright et al., "2006 consensus guidelines for the management of women with cervical intraepithelial neoplasia or adenocarcinoma in situ," *Am. J. Obstet. Gynecol.*, 197(4):340-345 (2007).

Wright et al., "2006 consensus guidelines for the management of women with cervical intraepithelial neoplasia or adenocarcinoma in situ," *J. Low Genit. Tract Dis.*, 11(4):223-239 (2007).

Wright et al., "Precancerous lesions of the cervix,"*Blausteins pathology of the female genital tract*, Kurman ed., 5th ed. New York: Springer, 253-324 (2002).

Wu et al., "Quantification of CYP1A1 and 1B1 mRNA in polycyclic aromatic hydrocarbon-treated human T-47D and HepG2 cells by a modified bDNA assay using fluorescence detection," Analytical Biochemistry, 312:162-166 (2003).

Yang et al., "BADGE, Beads Array for the Detection of Gene Expression, a high-throughput diagnostic bioassay," *Genome Res.*, 11(11):1888-1898 (2001).

Yang et al., "Sensitive detection of human papillomavirus in cervical, head/neck, and schistosomiasis-associated bladder malignancies," *Proc. Natl. Acad. Sci. U.S.A.*, 102(21):7683-7688 (2005).

Zhang et al., "Small interfering RNA and gene expression analysis using a multiplex branched DNA assay without RNA purification," *J. Biomolecular Screening*, 10(6):549-556 (2005).

Zolg et al., "High salt lysates: a simple method to stores blood samples without refrigeration for subsequent use with DNA probes," *Am. J. Trop. Med. Hyg.*, 39(1):33-40 (1988).

Moody et al., "Human papillomavirus oncoproteins: pathways to transformation," *Nat. Rev. Cancer*, 10(8):550-560 (2010).

\* cited by examiner

Figure 1. RNAscope

Figure 5. Comparison of RNAscope and RNAscope-TSA

Detecting mRNAs of low copy gene HPRT1 in human breast cancer FFPE sections with RNAscope and RNAscope + TSA procedures. Signal obtained with RNAscope + TSA (right) was significantly stronger than that obtained with RNAscope alone (left).

ULTRA SENSITIVE METHOD FOR IN SITU DETECTION OF NUCLEIC ACIDS

CROSS-REFERENCE TO RELATED APPLICATIONS

This application claims priority to and benefit of U.S. provisional patent application No. 61/405,503, filed on Oct. 21, 2010, entitled "ULTRA SENSITIVE METHOD FOR IN SITU DETECTION OF NUCLEIC ACIDS" by Wu et al., and U.S. provisional patent application No. 61/412,276, filed on Nov. 10, 2010, with entitled "ULTRA SENSITIVE METHOD FOR IN SITU DETECTION OF NUCLEIC ACIDS" by Wu et al. Each of these applications is incorporated herein by reference in its entirety for all purposes.

FIELD OF THE INVENTION

The invention relates generally to nucleic acid chemistry and biochemical assays. More particularly, the invention relates to methods for in situ detection of nucleic acid analytes in a sample.

BACKGROUND OF THE INVENTION

In situ hybridization (ISH) is a technique that allows detection and localization of specific nucleic acid molecules in morphologically preserved individual cells, histological tissue sections, or chromosome preparations. It was first described in 1969 and is based on the complementary hybridization of a nucleotide probe to a specific target sequence of DNA or RNA in the cell. This may be endogenous DNA, messenger RNA (mRNA), micro RNA (miRNA), viral sequences, or bacterial sequences. The added probe is labeled with a reporter molecule and sites of binding are visualized either fluorescently (Fluorescent in situ hybridization, FISH) or chromogenically (Chromogenic in situ hybridization, CISH).

After completion of sequencing the whole human genome, many thousands of novel human gene sequences have been annotated in public and private databases in recent years. This opened a new door for ISH, since it is relatively easy, fast and inexpensive to design and synthesizes antisense probes for detecting a specific sequence of any novel gene in the cell. The tissue-specific and cell-type specific express patterns together with expression level of the gene can be obtained with ISH, which will provide valuable information for analyzing the function of the gene.

However, the application of ISH techniques can be limited by their inability to detect DNA or RNA targets with low copy numbers in cells due to lack of sensitivity and specificity. It is especially challenging to apply ISH into the clinical setting where formalin fixation and paraffin embedding (FFPE) is the most commonly used method worldwide to store clinical tissue samples. The FFPE method preserves tissue morphology well but the cross-linking fixation by formaldehyde can cause poor accessibility of the target sequence to the detection probe, chemical or physical interaction of the probe molecules with other molecules or structures, and damage to nuclear acids, especially mRNAs.

Figure 1:
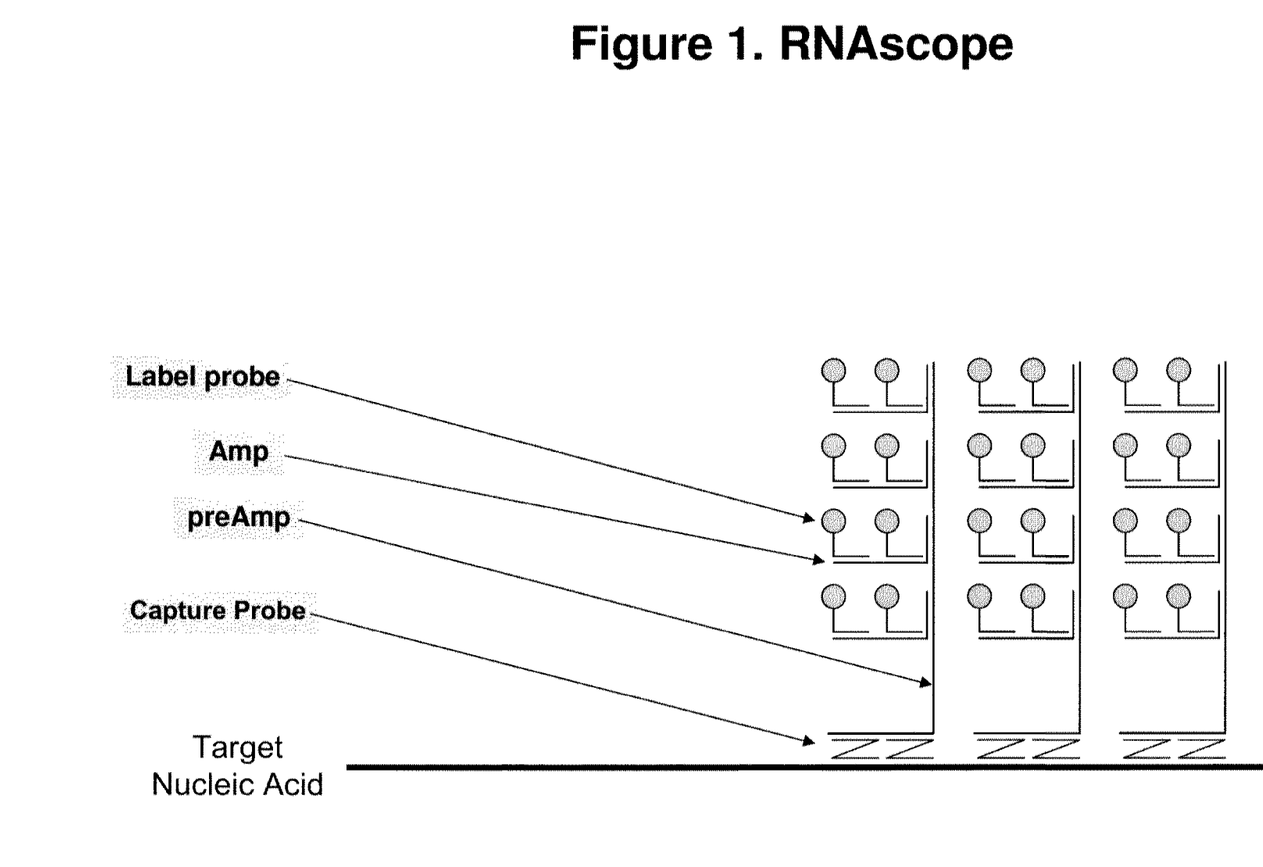
FIG. 1 illustrates the principle of the RNAscope® assay. A target nucleic acid such as mRNA are hybridized with sets of capture probes. Each set of capture probe comprises two or more capture probes. The set of capture probes is hybridized with a preamplifier. Each preamplifier is further hybridized with a plurality of amplifier. The signal is further amplified by hybridizing the amplifiers with multiple label probes. Each label probe is conjugated to one or more labels such as fluorophore or enzyme. Signals are detected using a standard bright-field or epifluorescent microscope.

In order to circumvent the limitation of ISH and extend its utility in diagnostic pathology, several strategies have been developed to improve the sensitivity of ISH. Recently, a new ISH signal amplification method called RNAscope® was developed by Advanced Cell Diagnostics, Inc. (U.S. Pat. No. 7,709,198). This assay includes uniquely designed oligo capture probes and a signal amplification system composed of preamplifiers, amplifiers, and label probes, allowing substantial signal amplification without amplifying background signal, enabling single RNA molecule detection for virtually any genes. An exemplary embodiment of the RNAscope® technology is schematically illustrated in FIG. 1 and will be described in detail in Section 2 of this application.

In a typical RNAscope® assay for detecting target nucleic acid, a target mRNA whose expression is to be detected is released from cells and captured on a solid surface (e.g., a well of a microtiter plate). A set of two or more capture probes and a signal generating multimer are also provided. The capture probes hybridize to both target nucleic acid and signal generating multimer and thus capture signal generating multimer to target nucleic acid. The signal generating multimer comprises label probes (LPs). But more typically, the signal generating multimer comprises preamplifiers and/or amplifiers in addition to label probes. The label probe is capable of binding to a label particle or molecule that provide detectable signal. The label probe has a larger molecular structure enabling that attachment of a plurality of label particle or molecules that provide stronger signal than a single label particle or molecule. Thus, RNAscope® improves the sensitivity and specific of nucleic acid detection.

However, RNAscope® alone still cannot reliably detect some low copy genes in retrospective Formalin-Fixed, Paraffin-Embedded (FFPE) tissue sections where RNA is significantly degraded. Also, single RNA molecule cannot to be visualized at 40× magnification using current RNAscope® technology. It is desirable to further enhance the detection signal to enable more robust detection of any RNA molecules, including the significantly degraded RNA molecules, and to allow easy visualization of detected RNA signal at 10× magnification.

Here we describe a novel ISH signal amplification assay to extend the utility of ISH in diagnostic pathology by combining two signal amplification methods into one system. This system has three formats: (1) RNAscope® in combination with biotin-(strept)avidin, (2) RNAscope® in combination with an antibody, (3) RNAscope® in combination with Tyramide Signal Amplification (TSA). All these methods can leverage the exceptional specificity of RNAscope® technology with the amplification power of the three amplification methods. We surprisingly found that the above three combined signal amplification methods can highly amplify signals associated with the presence of a target nucleic acid in sample while having excellent signal to noise ratio.

Biotin-avidin (or biotin-streptavidin) is a well known signal amplification system base on the facts that the two molecules have extraordinarily high affinity to each other and that one avidin/streptavidin molecule can bind four biotin molecules. Antibodies are widely used for signal amplification in immunohistochemistry and ISH. TSA is based on the deposition of a large number of haptenized tyramide molecules by peroxidase activity. Tyramine is a phenolic compound. In the presence of small amounts of hydrogen peroxide, immobilized Horse Radish Peroxidase (HRP) converts the labeled substrate into a short-lived, extremely reactive intermediate. The activated substrate molecules then very rapidly react with and covalently bind to electron-rich moieties of proteins, such as tyrosine, at or near the site of the peroxidase binding site. In this way, a lot of extra hapten molecules conjugated to tyramide can be introduced at the hybridization site in situ. Subsequently, the deposited tyramide-hapten molecules can be visualized directly or indirectly.

All of these signal amplification methods have been used in ISH with different degrees of success but usually the signal intensity and/or signal to noise ratio are not good enough for routine diagnostic pathology. In the case of ISA, in particular, when used alone in ISH, produces a high degree of background noise. The day-to-day and laboratory-to-laboratory consistency is also less than desirable.

In view of the above, a need exists for methods of amplifying nucleic acids with both high intensity and high specificity. A need also exists for such a method with strong consistency. The present invention provides these and other features that will be apparent upon review of the following.

SUMMARY OF THE INVENTION

The present invention combines the signal amplification method of RNAscope® with the general ISH signal amplification methods into a ultra sensitive method to detect, quantify and identify one or more target nucleic acid in a sample. The RNAscope® assay offers exceptional specificity owning to its unique paired capture probe design. By adding general ISH signal amplification methods such as the TSA-based signal amplification to the RNAscope® assay, the combined method achieves great signal intensity and low background. The signal amplification methods and system disclosed in this invention are relatively simple to use and produce consistent result. The claimed method can be easily adapted for use in routine clinic diagnostic procedures.

In a preferred embodiment of the present invention, the specificity and sensitivity of the disclosed signal amplification method are balanced. The balance is achieved by a moderate reduction of the fold of signal amplification in RNAscope®. In one embodiment of the present invention, one preamplifer is designed to bind between 1 to 16 amplifiers. In a preferred embodiment, one preamplifer is designed to bind between 2 to 10 amplifiers. In another more preferred embodiment, one preamplifer is designed to bind between 2 to 5 amplifiers.

In a preferred embodiment of detecting a target nucleic acid in a sample, the sample comprising or suspected of comprising the target nucleic acid is first provided, together with at least one set of two or more capture probes capable of hybridizing to the target nucleic acid, a signal generating multimer capable of hybridizing to the set of two or more capture probes, wherein said signal generating multimer comprises a label probe, and a signal amplification probe capable of binding to the label probe wherein the signal amplification probe comprises a label. In the method, the target nucleic acid is first hybridized to the set of two or more capture probes, then the signal generating multimer is captured to the set of two or more capture probes and thereby being captured the signal generating multimer to the target nucleic acid. The signal amplification probe is then captured to the label probe and thereby being captured to the signal generating multimer. In the last step, the presence, absence, or amount of the label in the signal amplification probe are detected.

In one embodiment, the signal amplification probe comprises: a biotin molecule which is capable of conjugating to the label probe, an avidin/streptavidin molecule which is capable of binding to the biotin molecule, and additional biotin molecules being conjugated to Horse Radish Peroxidase (HRP), Alkaline Phosphatase (AP), or fluorophore and are capable of binding to the avidin/streptavidin molecule.

In another embodiment, the signal amplification probe comprises: a HRP, AP, Dinitrophenyl (DNP), or fluorophore molecule which is capable of conjugating to the label probe, one or more first antibody which is capable of binding to said HRP, AP, DNP, or fluorophore molecule, and one or more second antibody being conjugated to HRP, Polymer-HRP, AP, Polymer-AP or fluorophore and is capable of binding to said one or more first antibody.

In yet another embodiment, the signal amplification probe comprises: a HRP molecule which is capable of conjugating to said label probe, a plurality of tyramide-biotin or tyramide-fluorophore molecules which are capable of reacting with said HRP molecule, and detection labels which are capable detecting said tyramide-biotin or tyramide-fluorophore molecules visually. The detection labels are a combination of avidin/streptavidin-HRP and a chromogenic substrate or a combination of avidin/streptavidin-AP and a chromogenic substrate. The chromogenic substrate is selected from the group consisting of: diaminobenzine (DAB) and Fast Red.

In one embodiment, the signal generating multimer comprises a label probe capable of hybridizing to the set of two or more capture probes. In another embodiment, the signal generating multimer comprises a label probe and an amplifier hybridized to the label probe. The amplifier is capable of hybridizing to said set of two or more capture probes. In a preferred embodiment, the signal generating multimer comprises a label probe, an amplifier hybridized to the label, and a preamplifier hybridized to one or more of the amplifier. The preamplifier is capable of hybridizing to said set of two or more capture probes.

The target nucleic acid can be any type, such as, e.g., DNA, cDNA, RNA, mRNA, rRNA, miRNA, siRNA and/or the like.

In one embodiment, the amplification can take place on a solid support before hybridization is performed.

Methods of the invention further provide a variety of ways to multiplex two or more target nucleic acids. For example, the sample may comprise a cell comprising or suspected of comprising two or more different target nucleic acids. The sample may also comprise two or more different cells, each comprising or suspected of comprising a different target nucleic acid.

The two different target nucleic acids can be detected using a dual-color chromogenic in situ hybridization (CISH) or a dual-color fluorescent in situ hybridization (FISH). In one embodiment, the dual-color CISH is performed using two different signal amplification probes, wherein the first signal amplification probe comprises: tyramide-biotin, streptavidin-HRP and DAB, and the second signal amplification probe comprises: anti-DNP-AP and Fast Red.

The present invention includes kits to practice the methods of the invention. The kits can include reagents to carry out the nucleic acid detection and provide conditions necessary to practice the methods of the invention. The kits include, e.g., A kit comprising: a target nucleic acid, one set of two or more capture probes capable of hybridizing to said target nucleic acid, a signal generating multimer capable of hybridizing to the set of two or more capture probes wherein the signal generating multimer comprises a label probe, and a signal amplification probe capable of binding to the label probe, wherein the signal amplification probe comprises a label.

In the one type of the kit, the signal amplification probe comprises: a biotin molecule which is capable of conjugating to said label probe, an avidin/streptavidin molecule which is capable of binding to said biotin molecule, and additional biotin molecules being conjugated to HRP, AP or fluorophores and are capable of binding to the avidin/streptavidin molecule.

In another type of kit, the signal amplification probe comprises: a HRP, AP, DNP, or fluorophore molecule which is capable of conjugating to the label probe, one or more first antibody which is capable of binding to the HRP, AP, DNP, or fluorophore molecule, and one or more second antibody being conjugated to HRP, Polymer-HRP, AP, Polymer-AP or fluorophore and is capable of binding to the one or more first antibody.

In yet another type of kit, the signal amplification probe comprises: a HRP molecule which is capable of conjugating to the label probe, a plurality of tyramide-biotin or tyramide-fluorophore molecules which are capable of reacting with said HRP molecule, and detection labels which are capable detecting the tyramide-biotin molecules visually. The detection labels may be a combination of avidin/streptavidin-HRP and a chromogenic substrate or a combination of avidin/streptavidin-AP and a chromogenic substrate. The chromogenic substrate may be selected from the group consisting of: DAB and Fast Red.

In one kit, the signal generating multimer comprises a label probe capable of hybridizing to the set of two or more capture probes. In another kit, the signal generating multimer comprises a label probe and an amplifier hybridized to the label probe. The amplifier is capable of hybridizing to said set of two or more capture probes. In a preferred kit, the signal generating multimer comprises a label probe, an amplifier hybridized to the label, and a preamplifier hybridized to one or more of the amplifier.

The preamplifier:amplifier ratio in the kit may be between 1-16, or preferably between 2-10 or between 2-5.

The kit of the invention can function in the multiplexing of multiple nucleic acid amplifications. The kit may be used for detecting nucleic acid targets in two or more different cells, each comprising or suspected of comprising a different target nucleic acid, or to detect two or more nucleic acid targets in one cell. The signal amplification probe in the kit may be either a dual-color chromogenic in situ hybridization (CISH) probe or a dual-color fluorescent in situ hybridization (FISH) probe. In case the dual-color CISH probes are used, the first signal amplification probe comprises: tyramide-biotin, streptavidin-HRP and DAB, and the second signal amplification probe comprises: anti-DNP-AP and Fast Red.

Definitions

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

The term "nucleic acid" (and the equivalent term "polynucleotide") encompasses any physical string of monomer units that can be corresponded to a string of nucleotides, including a polymer of nucleotides (e.g., a typical DNA or RNA polymer), peptide nucleic acids (PNAs), modified oligonucleotides (e.g., oligonucleotides comprising nucleotides that are not typical to biological RNA or DNA, such as 2'-O-methylated oligonucleotides), and the like. The nucleotides of the polynucleotide can be deoxyribonucleotides, ribonucleotides or nucleotide analogs, can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The polynucleotide can additionally comprise non-nucleotide elements such as labels, quenchers, blocking groups, or the like. The polynucleotide can be, e.g., single-stranded or double-stranded.

A "nucleic acid target" or "target nucleic acid" refers to a nucleic acid, or optionally a region thereof, that is to be detected.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

The term "gene" is used broadly to refer to any nucleic acid associated with a biological function. Genes typically include coding sequences and/or the regulatory sequences required for expression of such coding sequences. The term gene can apply to a specific genomic sequence, as well as to a cDNA or an mRNA encoded by that genomic sequence.

The term "antibody" is used herein in the broadest sense and covers fully assembled antibodies, antibody fragments which retain the ability to specifically bind to the antigen (e.g., Fab, F(ab')2, Fv, and other fragments), single chain antibodies, diabodies, antibody chimeras, hybrid antibodies, bispecific antibodies, humanized antibodies, and the like. The term "antibody" covers both polyclonal and monoclonal antibodies.

The term "biological sample" or "tissue sample" as used herein refers to a sample obtained from a biological subject, including sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, fractions and cells isolated from a mammal. Exemplary biological samples include but are not limited to cell lysate, a cell culture, a cell line, a tissue, an organ, an organelle, a biological fluid, and the like. Preferred biological samples include but are not limited to a skin sample, tissue biopsies, and the like.

The term "label probe" refers to an entity that binds to a target molecule, directly or indirectly, and enables the target to be detected, e.g., by a readout instrument. A label probe (or "LP") is typically a single-stranded polynucleotide that comprises one or more label which directly or indirectly provides a detectable signal. The label can be covalently attached to the polynucleotide, or the polynucleotide can be configured to bind to the label (e.g., a biotinylated polynucleotide can bind a streptavidin-associated label). The label probe can, for example, hybridize directly to a target nucleic acid, or it can hybridize to a nucleic acid that is in turn hybridized to the target nucleic acid or to one or more other nucleic acids that are hybridized to the nucleic acid. Thus, the label probe can comprise a polynucleotide sequence that is complementary to a polynucleotide sequence of the target nucleic acid, or it can comprise at least one polynucleotide sequence that is complementary to a polynucleotide sequence in a capture probe, amplifier, or the like.

A "label" is a moiety that facilitates detection of a molecule. Common labels in the context of the present invention include fluorescent, luminescent, light-scattering, and/or colorimetric labels. Suitable labels include enzymes and fluorescent moieties, as well as radionuclides, substrates, cofactors, inhibitors, chemiluminescent moieties, magnetic particles, and the like. Exemplary labels include: Horse Radish Peroxidase (HRP), Alkaline Phosphatase (AP), fluorophore, Dinitrophenyl (DNP), etc. Patents teaching the use of such labels include U.S. Pat. Nos. 3,817,837; 3,850,752; 3,939,350; 3,996,345; 4,277,437; 4,275,149; and 4,366,241. Many labels are commercially available and can be used in the context of the invention.

A "capture probe" is a polynucleotide that is capable of hybridizing to a target nucleic acid and capturing a label probe to that target nucleic acid. The target probe can hybridize directly to the label probe, or it can hybridize to one or more nucleic acids that in turn hybridize to the label probe; for example, the target probe can hybridize to an amplifier or a preamplifier. The target probe thus includes a first polynucleotide sequence that is complementary to a polynucleotide sequence of the target nucleic acid and a second polynucleotide sequence that is complementary to a polynucleotide sequence of the label probe, amplifier, preamplifier, or the like. The target probe is preferably single-stranded.

An "amplifier" is a molecule, typically a polynucleotide, that is capable of hybridizing to multiple label probes. Typically, the amplifier hybridizes to multiple identical label probes. The amplifier also hybridizes to at least one target probe or nucleic acid bound to a target probe. For example, the amplifier can hybridize to at least one target probe and to a plurality of label probes, or to a preamplifier and a plurality of label probes. The amplifier can be, e.g., a linear, forked, comb-like, or branched nucleic acid. As noted for all polynucleotides, the amplifier can include modified nucleotides and/or nonstandard internucleotide linkages as well as standard deoxyribonucleotides, ribonucleotides, and/or phosphodiester bonds. Suitable amplifiers are described, for example, in U.S. Pat. No. 5,635,352, U.S. Pat. No. 5,124,246, U.S. Pat. No. 5,710,264, and U.S. Pat. No. 5,849,481.

A "preamplifier" is a molecule, typically a polynucleotide, that serves as an intermediate between one or more target probes and amplifiers. Typically, the preamplifier hybridizes simultaneously to one or more target probes and to a plurality of amplifiers. Exemplary preamplifiers are described, for example, in U.S. Pat. No. 5,635,352 and U.S. Pat. No. 5,681,697.

A "ISH" or "in situ hybridization" refers to a type of hybridization that uses a labeled complementary DNA or RNA strand (i.e., probe) to localize a specific DNA or RNA sequence in a portion or section of tissue (in situ). The probe types are double stranded DNA (dsDNA), single stranded DNA (ssDNA), single stranded complimentary RNA (ss-cRNA), messenger RNA (mRNA), micro RNA (miRNA), and synthetic oligonucleotides.

A "FISH" or "fluorescent in situ hybridization" refers to a type of ISH with a fluorescent label.

A "CISH" or "chromogenic in situ hybridization" refers to a type of ISH with a chromogenic label.

A "general ISH signal amplification" assay or system refers to any ISH based in situ hybridization assay or system that can amplify the specific DNA or RNA sequence targeted by the method. It includes, but not limited to the three exemplary general ISH signal amplification systems disclosed in the present invention (i.e., biotin-based ISH, antibody-based ISH, and TSA-based ISH).

DETAILED DESCRIPTION

The present invention provides methods and systems for detecting the presence of a target nucleic acid with improved sensitivity and specificity in a sample. The invention combines RNAscope®® method with general ISH signal amplification methods such as the TSA-based signal amplification method, the antibody-based signal amplification method, or the Biotin-Avidin-based signal amplification method. The RNAscope® method is known for its high specificity in detecting a target nucleic acid. In other words, a target nucleic acid can be detected with high signal-to-noise ratio in an RNAscope® assay. Such high specificity, as will be explained in Section 2 below, are derived from the "double Z" probe design and the preamplifier-amplifier-label probe signal cascade design. General ISH signal amplification methods are known for their ability to boosting signal amplification of nucleic acid molecules. However, ISH signal amplification methods are also known for their high signal to noise ratio and their lack of consistency in the amplification assays.

The present invention combines the RNAscope® method with general ISH signal amplification methods and further adjust the amplification ratio between the amplifier and preamplifier in RNAscope®. Among other benefits, methods and systems of the present invention overcome the above noted disadvantages of the general ISH signal amplification methods while retaining the unique mechanisms for background noise reduction in RNAscope®. As a result the present invention is capable of reliably detecting nucleic acid targets with great sensitivity and specificity. Such enhancement increases the consistency among the results of nucleic acid detection to the level that can be implemented in diagnostic assays.

1. Detection of Target Nucleic Acid by a Combination of RNAscope® and General ISH Signal Amplification Methods This invention describes a novel, simple and ultra sensitive in suit hybridization method for detecting target nucleic acid in a sample. This method can be used in both fluorescent ISH (FISH) and chromogenic ISH (CISH) assays. The method is capable of detecting nuclear acids (DNA and RNA) immobilized in intact cells, tissue sections, tissue microarrays and cDNA microarrays.

1.1 General ISH Signal Amplification Methods

There are many ISH signal amplification methods which have been developed to detect DNA or RNA target. Three exemplary ISH signal amplification methods will be described below: (1) Biotin-(Strept)avidin-based ISH signal amplification: (2) Antibody-based ISH signal amplification, and (3) Tyramide Signal Amplification (TSA)-based ISH signal amplification. It is clear to a skilled artisan that any ISH signal amplification method can be used in the present invention in combination with the RNAscope®. Thus, these examples should be not considered as a limitation to the present invention.

Figure 2:
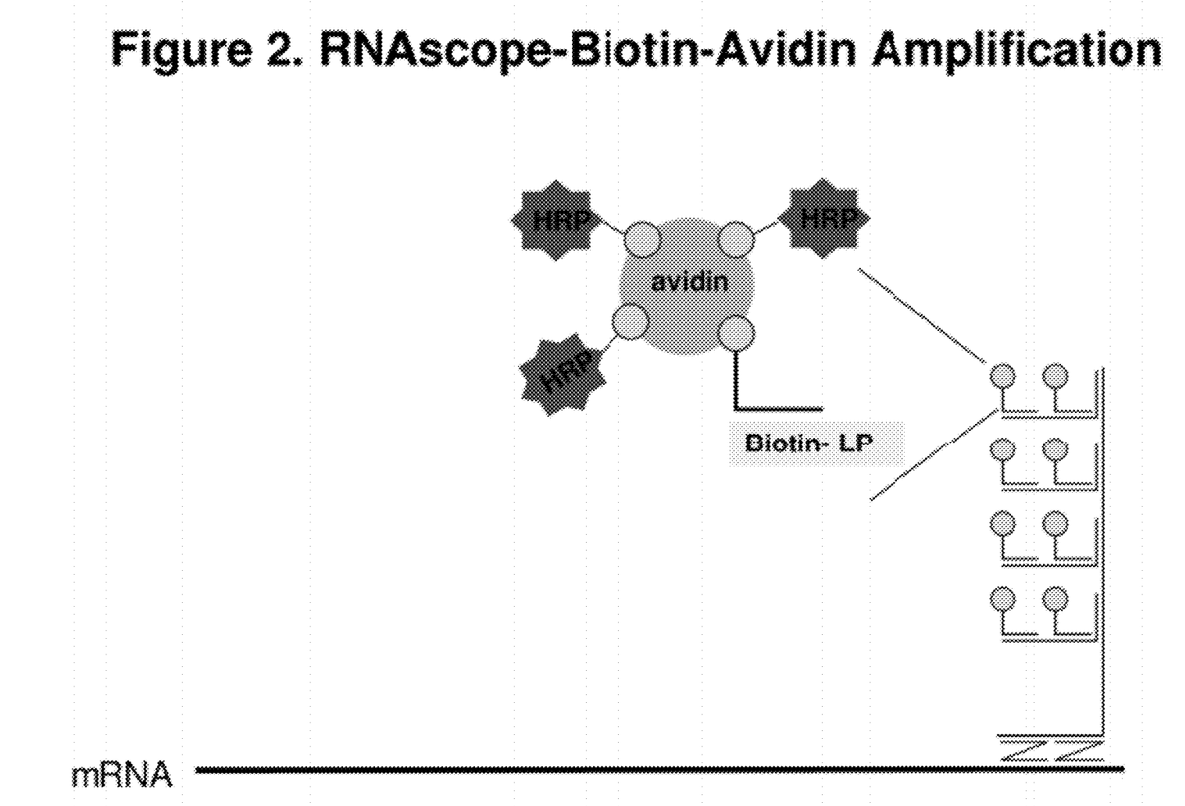
FIG. 2 illustrates the principle of RNAscope®+Biotin/(Strept)avidin amplification. Label probes in RNAscope® are conjugated to biotin molecules and further bound by avidin/streptavidin. Each avidin/streptavidin has the capacity of binding to a maximum of 4 biotin molecules which are conjugated to enzyme or fluorescent labels, such as Horse Radish Peroxidase (HRP), Alkaline Phosphatase (AP) or fluorophore, leading to a 4-fold increase in signal per label probe.

(1) RNAscope+Biotin-(Strept)Avidin System (FIG. 2).

In one embodiment, the biotin-(strept)avidin-based ISH signal amplification method was used in combination with RNAscope®. In one aspect, the RNAscope comprises a set of two or more capture probes, a plurality of label probes, a plurality of amplifiers, and a plurality of preamplifiers. The target nucleic acid is hybridized to the set of capture probes. The set of capture probes is then hybridized to a preamplifier. The preamplifier is further hybridized to a plurality of amplifiers. Each amplifier is then hybridized to a plurality of label probes. The label probe (LP) of the RNAscope complex structure is then conjugated to a biotin molecule of the ISH signal amplification structure and forms a LP-biotin complex. The LP-biotin complex is further bound by a avidin/streptavidin molecule. The avidin/streptavidin molecule has the capacity to bind a maximum of 4 biotin molecules where each biotin molecule is further conjugated to HRP or AP. HRP or AP can be detected visually by chromogenic dyes such as diaminobenzidine, DAB or Fast Red. Thus, combining biotin-(strept)avidin-based ISH signal amplification method with RNAscope® leads to a 4-fold increase in signal for every label probe.

Figure 3:
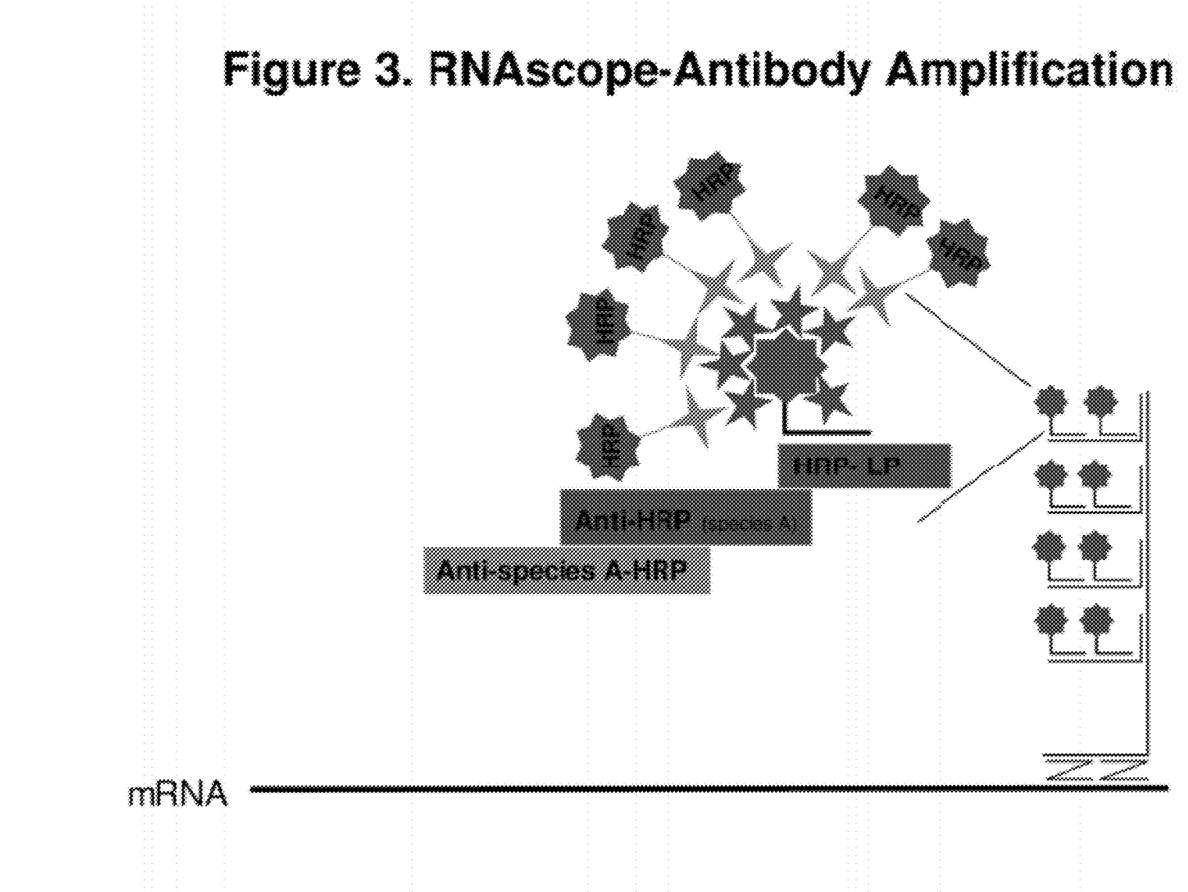
FIG. 3 illustrates the principle of RNAscope®+Antibody amplification. Label probes in RNAscope® are conjugated to HRP, AP, DNO, or fluorophore molecules and recognized by an antibody (produced in animal species A, such as goat) against HRP, AP, DNP, or fluorophore molecules. The first antibody then can be recognized by a HRP, polymer-HRP, AP, or polymer-AP conjugated secondary antibody against the first antibody of species A, leading to a further signal amplification of the RNAscope signal.

(2) RNAscope+Antibody System (FIG. 3).

In another embodiment, the antibody-based ISH signal amplification method was used in combination with RNAscope®. In one aspect, the RNAscope comprises a set of two or more capture probes, a plurality of label probes, a plurality of amplifiers, and a plurality of preamplifiers. The target nucleic acid is hybridized to the set of capture probes. The two or more capture probes are hybridized to the nucleic acid target. Every preamplifier are hybridized to each of the two or more capture probes, a plurality of amplifiers is hybridized to each of the preamplifiers, and the plurality of label probes is hybridized to the amplifiers. Each label probe of the RNAscope complex structure is conjugated to an HRP molecule, an AP molecule, a DNP molecule, or a fluorophore molecule and thus forming an HRP-LP complex, an AP-LP complex, a DNP-LP complex, or a fluorophore-LP complex, respectively. The HRP-LP, AP-LP, DNP-LP, or fluorophore-LP complex is recognized by an anti-HRP antibody, anti-AP-LP antibody, anti-DNP-LP antibody, or anti-fluorophore-LP antibody, respectively. The above antibodies are produced by animal species A, such as goat. This first antibody is then recognized by second antibody against species A. The second antibody is conjugated with HRP, Polymer-HRP, AP, Polymer-AP, or fluorophore and is capable of binding to one or more first antibodies. HRP or AP can be detected visually by chromogenic dyes such as Diaminobenzidine (DAB) or Fast Red. The result here is further signal amplification in addition to the RNAscope signal amplification.

Figure 4:
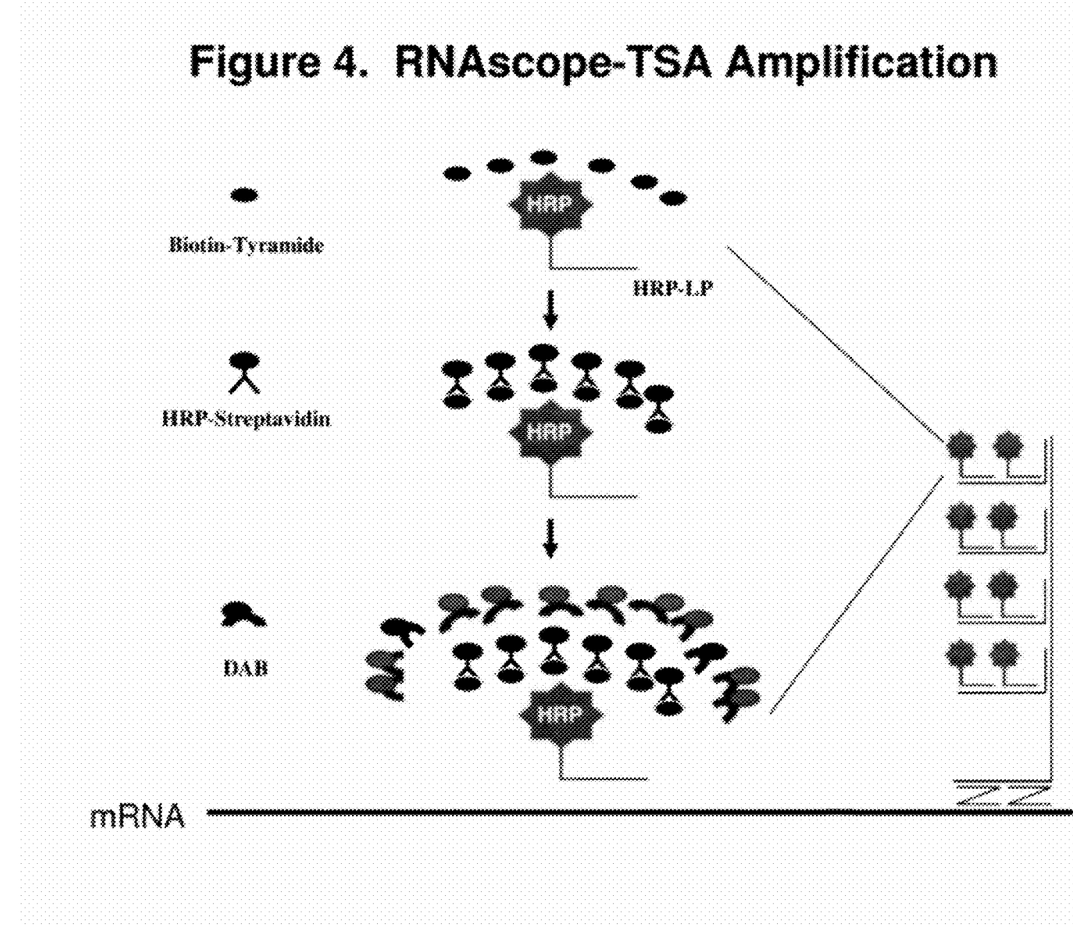
FIG. 4 illustrates the principle of RNAscope®+TSA amplification. Label probes in RNAscope® are conjugated to HRP. The HRP-conjugated label probes catalyze multiple copies of Tyramide-Biotin or Tyramide-Fluorophore to covalently bind to electron-rich moieties of proteins in the vicinity of LP-HRP binding sites. The Tyramide-Biotin or Tyramide-Fluorophore is then subsequently detected by avidin/streptavidin-HRP or avidin/streptavidin-AP together with chromogenic substrates for HRP or AP (such as DAB and Fast Red). Since many copies of tyramidebiotin can be deposited around each LP-HRP binding site, the intensity of end signal, which is the sum of RNAscope amplification and TSA amplification, is significantly increased.

(3) RNAscope+TSA System (FIG. 4).

In yet another embodiment, the TSA-based ISH signal amplification method was used in combination with RNAscope®. In one aspect, the RNAscope comprises a set of two or more capture probes, a plurality of label probes, a plurality of amplifiers, and a plurality of preamplifiers. The target nucleic acid is hybridized to the set of capture probes. The set of capture probes is then hybridized to a preamplifier. The preamplifier is further hybridized to a plurality of amplifiers. Each amplifier is then hybridized to a plurality of label probes. Each label probe of the RNAscope® complex structure is conjugated to an HRP molecule forming an HRP-LP complex. The HRP-LP complex is then bind to a plurality of Tyramide-Biotin or Fluorophore-Biotin molecules. In this step, the HRP-LP complex catalyze multiple copies of Tyramide-Biotin or Fluorophore-Biotin to covalently bind to electron-rich moieties of proteins in the vicinity of LP-HRP binding sites. The Tyramide-Biotin or Fluorophore-Biotin is then subsequently detected by detection labels. The detection labels are a combination of avidin/streptavidin-HRP and chromogenic substrate or a combination of avidin/streptavidin-AP and chromogenic substrate. The HRP or AP on the avidin/streptavidin-HRP or avidin/streptavidin-AP complexes are detected visually by chromogenic substrates such as DAB or Fast Red. Since many copies of Tyramide-Biotin or Fluorophore-Biotin can be deposited around each LP-HRP binding site, the intensity of end signal, which is the sum of RNAscope amplification and TSA amplification, is significantly increased.

In other embodiments of the TSA-based ISH signal amplification method, tyramide can also be conjugated to other haptens such as digoxigenin (DIG), trinitrophenyl (TNP), Dinotrophenyl (DNP) and fluorescent dyes. When fluorescent dye molecules are used in tyramide conjugation, the tyramide-dye conjugates can be directly used in RNAscope-TSA system for simple and effective fluorescent (FISH) detection.

1.2 Improving the Amplifier/Preamplifier Ratio in RNAscope®

The combination of RNAscope® with general ISH signal amplification methods disclosed in this invention can be further fine-tuned to increase the sensitivity and specificity of signal amplification. In this RNAscope®+general ISH signal amplification approach, RNAscope®'s major contribution is assay specificity. The RNAscope® also provides modest signal amplification of the nucleic acid target with high specificity. One of the general ISH signal amplification methods' contributions is their signal boosting power. Thus, in addition to the modest signal amplification power provided by RNAscope®, the general ISH signal amplification methods further amplify the target nucleic acid signal to a much higher level.

One potential problem is that the general ISH signal amplification methods not only amplify true positive signals, but also false positive signals. Thus a simple combination of RNAscope® with general ISH signal amplification methods faces the problem of elevated background noise in signal detection. The present invention discloses an intelligent way to reduce the level of false positive signals.

One balancing factor for the combination of RNAscope® with general ISH signal amplification methods disclosed in this invention is the size of the preamplifier used in RNAscope®. The preamplifier of the RNAscope® could be a very large molecule if it is designed to bind to a large number of amplifiers. For example, the preamplifier may have the capacity to hybridize to more than 20 amplifiers. Such a large molecule is prone to bind nonspecifically in cellular matrix during in situ hybridization. When one of the preamplifiers binds to sample nonspecifically, it will attract the same large number of amplifiers and label probes onto itself as it does when binding to a target nucleic acid. In the case when RNAscope® is used alone, the number of label probes which are bound to the few nonspecific binding preamplifiers may not generate any observable signals. However, if the signal of these label probes is further boosted by the additional signal amplification by a subsequent general ISH signal amplification, the false positive signal will be high enough to be detected.

One approach to reduce such false positive signal is to reduce the size of preamplifier so that, firstly, it is less likely to be trapped in cellular matrix; secondly, even when it is bound nonspecifically in the sample, only a smaller number of amplifier molecules will be hybridized to it. As a result, the signal produced by the nonspecific binding will likely be too low to be detected even when the signal is boosted by the general ISH signal amplification. In one embodiment of this approach, one preamplifier is designed to bind to between 1 to 16 amplifiers. In a more preferred embodiment, one preamplifier is designed to bind to between 2 to 10 amplifiers. In another preferred embodiment, one preamplifier is designed to bind to between 2 to 5 amplifiers.

Figure 5:
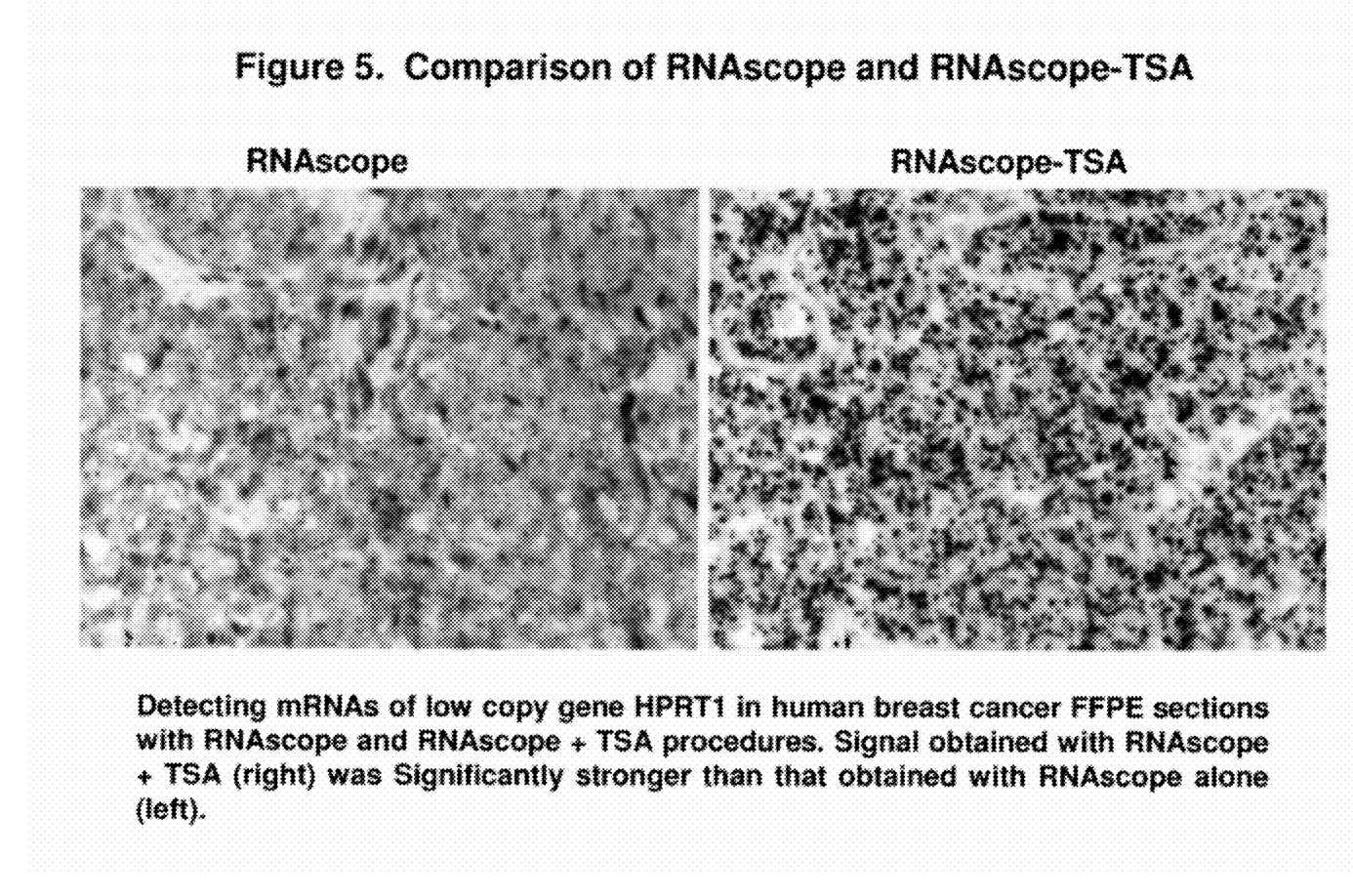
FIG. 5 illustrates detection of the mRNAs of low copy gene HPRT1 in human breast cancer FFPE sections using RNAscope and RNAscope+TSA procedures. Signal obtained with RNAscope+TSA (right) was significantly stronger than that obtained with RNAscope alone (left).

By balancing the amplification powers and specificity of RNAscope® and TSA in the assay, an optimum signal-to-noise ratio has been achieved for in situ RNA detection in routine clinical tissue specimen (see example 1 and FIG. 5).

2. Detection of Target Nucleic Acid by RNAscope®

A powerful in situ hybridization method called RNAscope® was recently developed by Advanced Cell Diagnostics, Inc. (U.S. Pat. No. 7,709,198, incorporated herein by reference in its entirety). Since RNAscope® is part of the method disclosed in the present invention, the working principle of RNAscope® will be described below for better understanding of the invention.

RNAscope® allows for direct visualization of RNA in situ. This method utilizes the oligonucleotide probe sets and novel signal amplification systems described below. The assay can be used on a variety of sample types including cultured cells, peripheral blood mononuclear cells (PBMCs), frozen tissue, and formalin-fixed paraffin embedded (FFPE) tissue. In addition, the assay can utilize both chromogenic and fluorescent detection reagents.

The RNAscope® assay technology provides multiplex nucleic acid assays in single cells (see FIG. 1). At the core of this technology is the "double Z" probe design, which allows robust amplification of specific hybridization signals without also amplifying nonspecific events. Each capture probe ("Z") has a target-specific sequence which binds to the target mRNA, a spacer, and a "tail" sequence. Two capture probes (double Z) hybridize contiguously onto a target mRNA, and the two "tail" sequences form a 28-base hybridization site for the preamplifier. The double Z probe design ensures high fidelity of signal amplification because: 1) it is highly unlikely that a pair of target probes will hybridize nonspecifically juxtaposed to each other to form a binding site for the preamplifier; and 2) neither tail alone can bind efficiently to the preamplifier under the assay conditions. The preamplifier, amplifier and label probe are hybridized sequentially to each capture probe pair, resulting in the accumulation of as many as 8,000 label molecules per 1 kb of target RNA. The label probe can be conjugated to either a fluorophore or a chromogenic enzyme (e.g., HRP or AP), enabling viewing of hybridization signals under a standard bright-field or epifluorescent microscope, respectively. With a fluorescent label probe, the signals can contain at least 100-fold more fluorescent molecules than traditional RNA fluorescent ISH methods and are readily visible under a standard fluorescent microscope.

In addition, multiple signal amplifiers have been built that each recognizes a unique tail sequence on the target probes, allowing for the simultaneous visualization of multiple target RNAs. Importantly, this assay is compatible with partially degraded RNA present in archival FFPE tissues, since the double Z probe pairs target short regions of ~50 nucleotides in length.

In one example, RNAscope® was used to detect a target nucleic acid. In the method, a sample comprising one or more cell is provided. The cell tested comprises, or is suspected of comprising, the target nucleic acid. Provided in the assay are: a set of capture probes comprising two or more capture probes, a label probe comprising a label, and optionally preamplifiers and amplifiers.

In the method, the set of capture probes is hybridized, in the cell, to the target nucleic acid. The label probe is captured to the set of capture probes, thereby capturing the label probe to the target nucleic acid. The signal from the label is then detected. Since the label is associated with the target nucleic acid through the capture probes, presence of the label(s) in the cell indicates the presence of the corresponding nucleic acid target(s) in the cell. The methods are optionally quantitative. Thus, an intensity of the signal can be measured, and the intensity of the signal can be correlated with a quantity of the target nucleic acid in the cell. As another example, a signal spot can be counted for each copy of the target nucleic acid in order to quantify them.

In one aspect, the label probes bind directly to the capture probes. In another aspect, the label probes are captured to the capture probes indirectly, for example, through binding of preamplifiers and/or amplifiers. Use of amplifiers and preamplifiers can be advantageous in increasing signal strength, since they can facilitate binding of large numbers of label probes to each nucleic acid target.

Although both direct capture approach and indirect capture approach can be used in the instant technology, the indirect capture approach is preferred because it enables the label probe to be target-independent and further disclosure will show that it can offer better specificity and sensitivity.

The capture probe is specially designed in the RNAscope® assay. In each capture probe, there is at least one section, T, complementary to a section on the target molecule, and another section. L, complementary to a section on the label probe. The T and L sections are connected by a section C. In a indirect capture embodiment, two adjacent capture probes are incorporated in a probe set targeting a gene of interest. T1 and T2 are designed to be complementary to two unique and adjacent sections on the target nucleic acid. L1 and L2, which can be different or the same, are complementary to two adjacent sections on the label probe. Their binding sections, T, L or both, are designed so that the linkage between the label probe and the target is unstable and tends to fall off at hybridization temperature when only one of the capture probes is in place. Such a design should enable exceptional specificity because the signal-generating label probe can only be attached to the target gene of interest when two independent capture probes both recognize the target and bind to the adjacent sequences or in very close proximity of the target gene. In one embodiment, the melting temperature, $T_m$, of the T sections of the two capture probes are designed to be significantly above the hybridization temperature while the $T_m$ of the L sections is below the hybridization temperature. As a result, T sections bind to the target molecule strongly and stably during hybridization, while L sections bind to the label probe weakly and unstably if only one of the capture probes is present. However, if both capture probes are present, the combination of L1 and L2 holds the label probe strongly and stably during hybridization. For example, the T sections can be 20-30 nucleotides in length while the L sections are 13-15 nucleotides in length; C can be 0 to 10 nucleotides in length, e.g., 5 nucleotides. In another embodiment, $T_m$ of the T sections is below hybridization temperature while $T_m$ of the L sections is substantially above. In the same way, the linkage between the label probe and the target can only survive the hybridization when both capture probes are hybridized to the target in a cooperative fashion. See U.S. Pat. No. 7,709,198 for additional details on design of capture probes.

In the above classes of embodiments, the capture probes preferably hybridize to nonoverlapping polynucleotide sequences in their respective nucleic acid target. The capture probes can, but need not, cover a contiguous region of the nucleic acid target. Blocking probes, polynucleotides which hybridize to regions of the nucleic acid target not occupied by target probes, are optionally provided and hybridized to the target. For a given nucleic acid target, the corresponding capture probes and blocking probes are preferably complementary to physically distinct, nonoverlapping sequences in the nucleic acid target, which nonoverlapping sequences are preferably, but not necessarily, contiguous. Having the capture probes and optional blocking probes be contiguous with each other can in some embodiments enhance hybridization strength, remove secondary structure, and ensure more consistent and reproducible signal.

In detection of nucleic acid targets in a cell, the cell is typically fixed and permeabilized before hybridization of the capture probes, to retain the nucleic acid targets in the cell and to permit the capture probes, label probes, etc. to enter the cell. The cell is optionally washed to remove materials not captured to one of the nucleic acid targets. The cell can be washed after any of various steps, for example, after hybridization of the capture probes to the nucleic acid targets to remove unbound capture probes, after hybridization of the preamplifiers, amplifiers, and/or label probes to the capture probes, and/or the like.

In some embodiments, the cell is in suspension for all or most of the steps of the method, for ease of handling. However, the methods are also applicable to cells in solid tissue samples (e.g., tissue sections) and/or cells immobilized on a substrate (e.g., a slide or other surface). Thus, in one class of embodiments, the cell is in suspension in the sample comprising the cell, and/or the cell is in suspension during the hybridizing, capturing, and/or detecting steps. For example, the cell can be in suspension in the sample and during the hybridization, capture, optional washing, and detection steps. In other embodiments, the cell is in suspension in the sample comprising the cell, and the cell is fixed on a substrate during the hybridizing, capturing, and/or detecting steps. For example, the cell can be in suspension during the hybridization, capture, and optional washing steps and immobilized on a substrate during the detection step. In other embodiments, the sample comprises a tissue section.

3. Multiplexing Detection of Nucleic Acids

One aspect of the invention provides multiplex nucleic acid assays. Thus, one general class of embodiments includes methods of detecting two or more target nucleic acids. In the section above, method for detecting a single target nucleic acid using RNAscope® has been described. In this section, method for detecting a single target nucleic acid using a combination of RNAscope® and general ISH signal amplification method will be described first. Method for detecting two or more target nucleic acids using a combination of RNAscope® and general ISH signal amplification method will be described next. The detection of two or more target nucleic acids can be conducted in a same way as that of detecting a single target nucleic acids except for using different, target-specific, labels and probes.

In one embodiment of the invention, a method of detecting a single target nucleic acid is provided. In this method, a sample comprising or suspected of comprising the target nucleic acid is provided. Also provided are: a set of two or more capture probes wherein the capture probes are capable of binding to the target nucleic acid, signal generating multimers, and signal amplification probes.

The signal generating multimer comprises at least a label probe. In a preferred embodiment, the signal generating multimer comprises a label probe and an amplifier. The amplifier is capable of hybridizing to the label probe, and is also capable of hybridizing to the set of two or more capture probes. In another preferred embodiment, the signal generating multimer comprises a label probe, an amplifier capable of hybridizing to the label, and a preamplifier capable of hybridizing to the amplifier and also capable of hybridizing to the set of two or more capture probes.

The signal amplification probes are made of components used in general ISH signal amplification assays. For example, in an embodiment where RNAscope® is combined with a biotin-strept(avidin) based ISH assay, the signal amplification probe comprises: a biotin molecule which is capable of conjugating to the label probe of RNAscope®, an avidin/streptavidin molecule which is capable of binding to the biotin molecule, and additional biotin molecules being conjugated to HRP, AP, or fluorophore and are capable of binding to the avidin/streptavidin molecule.

In an embodiment where RNAscope® is combined with a antibody-based ISH assay, the signal amplification probe comprises: a HRP, DNP, fluorophore, or AP molecule which is capable of conjugating to said label probe, one or more first antibody which is capable of binding to the HRP, DNP, fluorophore, or AP molecule, and one or more second antibody which is conjugated with HRP, Polymer-HRP, AP, or Polymer-AP and is capable of binding to one or more of the first antibody.

In an embodiment where RNAscope® is combined with a ISA-based ISH assay, the signal amplification probe comprises: a HRP molecule which is capable of conjugating to said label probe, a plurality of tyramide-biotin or tyramide-fluorophore molecules which are capable of reacting with the HRP molecule, and detection labels which are capable binding to the tyramide-biotin or tyramide-fluorophore molecules and thus display the target nucleic acid visually. The detection labels are a combination of acivdin/strepavidin-HRP and a chromogenic substrate or a combination of acivdin/strepavidin-HRP and a chromogenic substrate.

In the method of detecting a target nucleic acid, a sample comprising or suspected of comprising the target nucleic acid is first provided. The target nucleic acid is then hybridized to the set of two or more capture probes. The signal generating multimer is then added and being hybridized to the set of two or more capture probes and thereby being captured to the target nucleic acid. Components of the signal amplification probe are then added to the assay solution sequentially and bind to the signal generating multimer and thereby being captured to the target nucleic acid. The labels in the signal amplification probe are then detected by flow cytometer or other visualization devices. The presence, absence, or amount of the labels allows a sensitive detection and localization of the target nucleic acid in the sample.

In the method of detecting two target nucleic acids, a sample comprising or suspected of comprising the two target nucleic acids is provided. Also provided are two or more sets of capture probes, each set comprising two or more capture probes. The first set of capture probe is capable of hybridizing to the first target nucleic acid but not the second target nucleic acid, and the second set of capture probe is capable of hybridizing to the second target nucleic acid but not the first target nucleic acid. Further provided are a first signal generating multimer and a first signal amplification probe, together with a second signal generating multimer and a second signal amplification probe.

The first signal generating multimer can hybridize to the first set of capture probe but not the second set of capture probe. The second signal generating multimer can hybridize to the second set of capture probe but not the first set of capture probe. The first signal generating multimer has a first label probe that hybridize, either directly or indirectly through preamplifiers and amplifiers, to the first set of capture probe. The second signal generating multimer has a second label probe that hybridize, either directly or indirectly through preamplifiers and amplifiers, to the second set of capture probe. The first label probe is different from the second label probe.

The first signal generating multimer and the second signal generating multimer are labeled with different signal amplification probes sequentially. The two signal amplification probes can be a dual-color CISH or a dual-color FISH.

At least three steps will be performed in a duplex nucleic acid detection. In the first step, the first signal generating multimer is labeled with the first signal amplification probe. In an exemplary embodiment, the first signal amplification probe is a TSA-based ISH signal amplification which linked with the label probe of RNAscope® amplification via a conjugated LP-HRP complex. After the RNAscope® method is performed, the label probe of RNAscope® is first conjugated with HRP. The conjugated LP-HRP complex is then detected with sequential incubation of tyramide-biotin, streptavidin-HRP and color substrate DAB, resulting in brown signal for the first target nucleic acid. In the second step, the residual labeling agents for the first signal generating multimer are blocked in order to prevent the labels from reacting with the second signal generating multimer which is going to be added in the third step. In the third step, the second signal generating multimer is labeled with the second signal amplification probe. In an exemplary embodiment, After the RNAscope® method is performed, the label probe of RNAscope® is first conjugated with Dinotrophenyl (DNP). The conjugated LP-DNP complex is then detected with sequential incubation of anti-DNP-AP and color substrate Fast Red, resulting in red signal for the first target nucleic acid.

The above methods are also useful for multiplex detection of nucleic acids, including sequential detection of more than three nucleic acid targets. Thus, the cell optionally comprises or is suspected of comprising a third, fourth, fifth, sixth, seventh or even more nucleic acid target can be analyzed in the similar way described above.

4. Kits

Yet another general class of embodiments provides a kit for detecting one or more target nucleic acid. In one aspect, the kit includes a target nucleic acid, an RNAscope® component and a general ISH signal amplification component. In one embodiment, the kit includes a target nucleic acid, sets of capture probes capable of hybridizing to the target nucleic acid, a signal generating multimer capable of hybridizing to set of capture probes, and a signal amplification probe capable of binding to the label probe. The signal generating multimer comprises a label probe and the signal amplification probe comprises a label. In certain embodiment, the signal generating multimer in the kit can include appropriate amplifiers, preamplifiers. The kit may also include a solid support. The ISH signal amplification component of the kit can be any ISH signal amplification system. For example, it can be the three ISH signal amplification systems described in Section 1.1 of the present invention. The kit can be used for detection of any nucleic acids described earlier in this application, including, not not limited to DNA, cDNA, RNA, and mRNA.

In multiplexed embodiments of kits, many components can be represented with two or more different subsets. For example, the label probes can include two subsets, hybridizing to the first and the second target nucleic acids, respectively. The signal generating multimer can include two different label probe, each hybridizes, either directly or indirectly, to the first and the second capture probes. The kit can also include two different signal amplification probes, each conjugates to the first and second label probes. The different signal amplification probes are distinguishable from each other by binding to different color substrates. In another aspect, the kit includes a blocking agent which is capable of blocking the residual labeling agents for the first signal generating multimer and thus ensuring the specific binding of the second signal generating multimer to the second target nucleic acid.

EXAMPLES

The following examples are offered to illustrate, but not to limit the claimed invention.

The following example shows how a combination of RNAscope® and general ISH signal amplification methods further enhanced by an optimized preamplifier/amplifier ratio achieves a significantly improved specificity and sensitivity for in situ RNA detection.

Example 1

RNAscope®+General ISH Signal Amplification Assay

The basic assay procedure can be done within a day and generally includes the following steps. A sample containing a plurality of cells suspected of comprising a target nucleic acid HPRT1 is provided. After being fixed and permeabilized, cells either fixed on a solid support or in suspension are hybridized to the following series of oligonucleotide probes. First, a set of capture probes is hybridized to the target RNA inside the cells. Next, preamplifier molecules are hybridized to the capture probes, providing a bridge for the hybridization of amplifier molecules. Multiple amplifier molecules are further hybridized to a preamplifier, e.g., up to 20 amplifiers to each preamplifier. Multiple label probes are then hybridized to an amplifier, e.g. up to 20 label probes to each amplifier.

The signal intensity is enhanced further by TSA-based ISH signal amplification. An HRP is conjugated to each label probe. Reagent containing tyramide-biotin molecules is then added to the assay solution. The HRP-conjugated-label-probe catalyzes multiple copies of tyramide-biotin to covalently bind to the electron-rich moieties of proteins in the vicinity of the HRP-label probe binding site. The tyramide-biotin molecule is then detected by avidin/streptavidin-HRP, where avidin/streptavidin-HRP can be visualized by label substrate DAB which shows brown color. Signals are detected, e.g., with either a regular fluorescent microscope with appropriate filters or with a multicolor flow cytometer. A comparison of detection of mRNA of low copy gene HPRT1 gene in human breast cancer FFPE sections, either with RNAscope® alone or RNAscope®+TSA-based ISH signal amplification, were made. As shown in FIG. 5, signals obtained from RNAscope®+TSA-based ISH signal amplification method was significantly stronger than that obtained from RNAscope® alone.

Nonspecific binding was prevented or minimized by designing probe sets targeting a specific mRNA sequence using a double "Z" probe design. The double "Z" capture probes were designed based on the sequence of the HPRT1 and were prescreened against the GenBank database to ensure minimal cross-hybridization with unintended nucleic acid sequences. In the double design, two neighboring probes each contain a target-hybridizing sequence, e.g., 20 to 30 base in length with a $T_m$ significantly above the assay temperature, and a preamplifier-hybridizing sequence, e.g., only 14 bases in length with a $T_m$ well below the assay temperature. As a result, a single capture probe is able to bind to target RNA strongly and stably during hybridization, but will bind to the preamplifier weakly and unstably due to the 14 base pair region of homology having a $T_m$ well below the assay temperature. However, when two capture probes are present in neighboring positions, the combined hybridization strength, e.g., of 28 complementary base pairs, holds the preamplifier strongly and stably at the assay temperature, enabling signal amplification to occur. Such a double "Z" design ensures high detection specificity and simplifies probe design for simultaneous detection of multiple targets.

Due to the signal boosting power of the TSA-based ISH signal amplification method, the nonspecific binding of preamplifier in cellular matrix during in situ hybridization could be amplified and consequently produces a false positive signal. This problem becomes serious when the preamplifier is designed to bind large number of amplifiers and thus is large in size. Power of amplification is gained at the cost of lost binding specificity. We solved this problem by moderately reducing the number of amplifiers a preamplifier is designed to bind to. The end result is increased the signal-to-noise ratio. The lost amplification power is compensated by signal boosting power of the ISH signal amplification methods, particularly the TSA-based ISH signal amplification method.

Several amplifiers have been designed and tested in this assay. Preamplifier PREAMP1 is designed to bind to 20 amplifiers. Preamplifier PREAMP2 is designed to bind to 16 amplifiers. Preamplifier PREAMP3 is designed to bind to 10 amplifiers. Preamplifier PREAMP4 is designed to bind to 5 amplifiers.

Experimental results show that PREAMP2 has improved signal-to-noise ratio over PREAMP1. PREAMP3 and PREAMP4 have the best signal-to-noise ratio among all the PREAMPs tested (data not shown).

Example 2

Multiplex RNAscope®+General ISH Signal Amplification Assay

The following prophetic example of a multiplexed amplification showing how the method disclosed in the present invention can detect two target nucleic acids with high sensitivity. To explore the potential of the disclosed invention for in situ detection of low copy RNA transcripts and its capability for multiplex detection, 18S and Her-2 are used as the model genes.

In the first amplification, 18S gene is captured on capture probes designed for 18S. The capture probe for 18S is designed as described in example 1. The capture-probe-hybridized-18S gene is then sequentially hybridized to preamplifiers, amplifiers and label probes. The label probe is then conjugated to HRP. The conjugated LP-HRP complexes are then detected with sequential incubations of tyramide-biotin, streptavidin-HRP and DAB. The product of the hybridization produces brown color at locations where target gene 18Ss are detected.

Before starting the second amplification, the residue HRPs from the first amplification are blocked. In the second amplification, Her-2 gene is captured on capture probes designed for Her-2. The capture probe for Her-2 is designed as described in example 1. The capture-probe-hybridized-Her-2 gene is then sequentially hybridized to preamplifiers, amplifiers and label probes. The label probe is then conjugated to Diotrophenyl (DNP). The conjugated LP-DNPs are then detected with incubation of anti-DNP-AP. The alkaline phosphatase (AP) molecule on the anti-DNP-AP complex is then detected by dye reagent Fast Red. The product of the hybridization produces red signal for target gene Her-2.

In this example we have demonstrated that the method disclosed in this invention can be used to detect two RNA transcripts. The relative intensity of the signals can be used to compare gene expression levels of the two genes.

What is claimed is:

1. A method of detecting at least one target nucleic acid, the method comprising:
    (a) providing a sample comprising or suspected of comprising said target nucleic acid;
    (b) providing at least one set of two or more capture probes capable of hybridizing to said target nucleic acid;
    (c) providing:
        (i) an amplifier capable of hybridizing to a label probe;
        (ii) a preamplifier capable of hybridizing to the amplifier and capable of hybridizing to said set of two or more capture probes, wherein the preamplifier:amplifier ratio is between 1:1-16, between 1:2-10, or between 1:2-5;
        (iii) a label probe, wherein the label probe is conjugated to a horse radish peroxidase (HRP) molecule; and
        (iv) a plurality of tyramide-fluorophore molecules, or a plurality of tyramide-biotin or tyramide-hapten molecules and detection labels which are capable of detecting said tyramide-biotin or tyramide-hapten molecules, wherein said tyramide is capable of reacting with said HRP molecule;
    (d) hybridizing said set of two or more capture probes to said target nucleic acid;
    (e) capturing the preamplifer, amplifer and label probe to said set of two or more capture probes, thereby capturing the label probe to said target nucleic acid; and
    (f) detecting the presence, absence, or amount of the fluorophore or detection label associated with the captured label probe.

2. The method of claim 1, wherein said detection labels comprise avidin/streptavidin-HRP and a chromogenic substrate or avidin/streptavidin-alkaline phosphatase (AP) and a chromogenic substrate.

3. The method of claim 2, wherein said chromogenic substrate is selected from the group consisting of: diaminobenzidine (DAB) and Fast Red.

4. The method of claim 1, wherein said target nucleic acid is selected from the group consisting of: a DNA, a cDNA, an RNA, an mRNA, an rRNA, an miRNA and an siRNA.

5. The method of claim 1, further comprising the step of capturing said target nucleic acid on a solid support.

6. The method of claim 1, wherein said sample comprises a cell comprising or suspected of comprising the target nucleic acid.

7. The method of claim 1, wherein said sample comprises a cell comprising or suspected of comprising two or more different target nucleic acids.

8. The method of claim 1, wherein said sample comprises two or more different cells, each comprising or suspected of comprising a different target nucleic acid.

9. The method of claim 7 or 8, wherein the two different target nucleic acids are detected using dual-color chromogenic in situ hybridization (CISH) or dual-color fluorescent in situ hybridization (FISH).

10. The method of claim 9, wherein said dual-color CISH is performed using tyramide-biotin, streptavidin-HRP and DAB to detect the first target nucleic acid, and an anti-DNP antibody conjugated to alkaline phosphatase (AP) and Fast Red to detect the second target nucleic acid.

11. The method of claim 1, wherein said hapten is selected from Dinitrophenyl (DNP), digoxygenin, trinitrophenyl (TNP), or a fluorophore.

12. The method of claim 1, wherein a plurality of tyramide-fluorophore molecules are provided.

13. The method of claim 1, wherein a plurality of tyramide-biotin molecules and detection labels which are capable of detecting said tyramide-biotin molecules are provided.

14. The method of claim 13, wherein said detection labels comprise avidin/streptavidin.

15. The method of claim 14, wherein said avidin/streptavidin is conjugated to HRP, polymer-HRP, AP, polymer-AP or a fluorophore.

16. The method of claim 15, wherein said detection labels comprise a chromogenic substrate.

17. The method of claim 16, where said chromogenic substrate is selected from DAB and Fast Red.

18. The method of claim 16, wherein said detection labels comprise avidin/streptavidin-HRP.

19. The method of claim 18, wherein the detection labels comprise avidin/streptavidin-HRP and DAB.

20. The method of claim 16, wherein said detection labels comprise avidin/streptavidin-AP.

21. The method of claim 20, wherein the detection labels comprise avidin/streptavidin-AP and Fast Red.

22. The method of claim 1, wherein a plurality of tyramide-hapten molecules and detection labels which are capable of detecting said tyramide-hapten molecules are provided.

23. The method of claim 22, wherein said detection labels comprise an anti-hapten antibody.

24. The method of claim 23, wherein said detection labels further comprise a second antibody, wherein said second antibody is capable of binding to said anti-hapten antibody and wherein said second antibody is conjugated to HRP, polymer-HRP, AP, polymer-HRP or a fluorophore.

25. The method of claim 24, wherein the second antibody is conjugated to a fluorophore.

26. The method of claim 24, wherein said detection labels comprise a chromogenic substrate.

27. The method of claim 26, where said chromogenic substrate is selected from DAB and Fast Red.

28. The method of claim 26, wherein said second antibody is conjugated to HRP.

29. The method of claim 28, wherein the chromogenic substrate is DAB.

30. The method of claim 26, wherein said second antibody is conjugated to AP.

31. The method of claim 30, wherein the chromogenic substrate is Fast Red.

32. A kit comprising:
(a) at least one set of two or more capture probes capable of hybridizing to a target nucleic acid;
(b) an amplifier capable of hybridizing to a label probe;
(c) a preamplifier capable of hybridizing to the amplifier and capable of hybridizing to said set of two or more capture probes, wherein the preamplifier:amplifier ratio is used between 1:1-16, between 1:2-10, or between 1:2-5;
(d) a label a label probe, wherein the label probe is conjugated to a HRP molecule; and
(e) a plurality of tyramide-fluorophore molecules, or a plurality of tyramide-biotin or tyramide-hapten molecules and detection labels which are capable of detecting said tyramide-biotin or tyramide-hapten molecules.

33. The kit of claim 32, wherein said detection labels comprise avidin/streptavidin-HRP and a chromogenic substrate or avidin/streptavidin-AP and a chromogenic substrate.

34. The kit of claim 33, wherein said chromogenic substrate is selected from the group consisting of: DAB and Fast Red.

35. The kit of claim 32, wherein said target nucleic acid is selected from the group consisting of: a DNA, a cDNA, an RNA, an mRNA, an rRNA, an miRNA and an siRNA.

36. The kit of claim 32, further comprising the target nucleic acid.

37. The kit of claim 32, comprising two sets of two or more capture probes, each set capable of hybridizing to a different target nucleic acid.

38. The kit of claim 36 or 37, wherein said kit comprises reagents for dual-color chromogenic in situ hybridization (CISH) or dual-color fluorescent in situ hybridization (FISH) for detecting two different target nucleic acids.

39. The kit of claim 38, wherein said dual-color CISH reagents comprise tyramide-biotin, streptavidin-HRP and DAB for detecting the first target nucleic acid, and an anti-DNP antibody conjugated to alkaline phosphatase and Fast Red for detecting the second target nucleic acid.

40. The kit of claim 32, wherein said hapten is selected from Dinitrophenyl (DNP), digoxygenin, trinitrophenyl (TNP), or a fluorophore.

41. The kit of claim 32, wherein the kit comprises a plurality of tyramide-fluorophore molecules.

42. The kit of claim 32, wherein the kit comprises a plurality of tyramide-biotin molecules and detection labels which are capable of detecting said tyramide-biotin molecules.

43. The kit of claim 42, wherein said detection labels comprise avidin/streptavidin.

44. The kit of claim 43, wherein said avidin/streptavidin is conjugated to HRP, polymer-HRP, AP, polymer-AP or a fluorophore.

45. The kit of claim 44, wherein said detection labels comprise a chromogenic substrate.

46. The kit of claim 45, where said chromogenic substrate is selected from DAB and Fast Red.

47. The kit of claim 45, wherein said detection labels comprise avidin/streptavidin-HRP.

48. The kit of claim 47, wherein the detection labels comprise avidin/streptavidin-HRP and DAB.

49. The kit of claim 45, wherein said detection labels comprise avidin/streptavidin-AP.

50. The kit of claim 49, wherein the detection labels comprise avidin/streptavidin-AP and Fast Red.

51. The kit of claim 32, wherein the kit comprises a plurality of tyramide-hapten molecules and detection labels which are capable of detecting said tyramide-hapten molecules.

52. The kit of claim 51, wherein said detection labels comprise an anti-hapten antibody.

53. The kit of claim 52, wherein said detection labels further comprise a second antibody, wherein said second antibody is capable of binding to said anti-hapten antibody and wherein said second antibody is conjugated to HRP, polymer-HRP, AP, polymer-HRP or a fluorophore.

54. The kit of claim 53, wherein the second antibody is conjugated to a fluorophore.

55. The kit of claim 53, wherein said detection labels comprise a chromogenic substrate.

56. The kit of claim 55, where said chromogenic substrate is selected from DAB and Fast Red.

57. The kit of claim 55, wherein said second antibody is conjugated to HRP.

58. The kit of claim 57, wherein the chromogenic substrate is DAB.

59. The kit of claim 55, wherein said second antibody is conjugated to AP.

60. The kit of claim 59, wherein the chromogenic substrate is Fast Red.

* * * * *